(12) United States Patent
Hansford

(10) Patent No.: US 10,309,912 B2
(45) Date of Patent: *Jun. 4, 2019

(54) METHODS AND APPARATUS FOR X-RAY DIFFRACTION

(71) Applicant: University of Leicester, Leicester (GB)

(72) Inventor: Graeme Mark Hansford, Coalville (GB)

(73) Assignee: University of Leicester, Leicester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/919,496

(22) Filed: Mar. 13, 2018

(65) Prior Publication Data

US 2018/0202950 A1 Jul. 19, 2018

Related U.S. Application Data

(63) Continuation of application No. 14/394,971, filed as application No. PCT/GB2013/050962 on Apr. 15, (Continued)

(30) Foreign Application Priority Data

Aug. 10, 2012 (GB) .................... 1214344.2

(51) Int. Cl.
  *G01N 23/20* (2018.01)
  *G01N 23/20091* (2018.01)
  (Continued)

(52) U.S. Cl.
  CPC ..... *G01N 23/20091* (2013.01); *G01N 23/203* (2013.01); *G01N 23/223* (2013.01); *G01N 2223/076* (2013.01)

(58) Field of Classification Search
  CPC ....... G01N 2223/076; G01N 23/20091; G01N 23/203; G01N 23/223
  See application file for complete search history.

(56) References Cited

U.S. PATENT DOCUMENTS 4,048,496 A * 9/1977 Albert .................. G01N 23/223
378/113
5,077,771 A * 12/1991 Skillicorn ............... H01J 35/16
378/102

(Continued)

FOREIGN PATENT DOCUMENTS

EP        0108447 A2    5/1984
EP        0911627 A1    4/1999
(Continued)

OTHER PUBLICATIONS

Hansford, Graeme Mark. "Back-reflection energy-dispersive X-ray diffraction: a novel diffraction technique with almost complete insensitivity to sample morphology." Journal of Applied Crystallography 44, No. 3 (Jun. 2011): 514-525.*

(Continued)

*Primary Examiner* — Wyatt A Stoffa
(74) *Attorney, Agent, or Firm* — Winstead PC

(57) ABSTRACT

Methods and apparatus are provided for performing back-reflection energy-dispersive X-ray diffraction (XRD). This exhibits extremely low sensitivity to the morphology of the sample under investigation. As a consequence of this insensitivity, unprepared samples can be analyzed using this method. For example, in a geological context, whole rock samples become amenable to analysis. A composite diffraction spectrum can be produced using information from different recorded spectra in different energy sub-ranges. The composite spectrum excludes fluorescence signals that would otherwise obscure the diffraction signals.

10 Claims, 16 Drawing Sheets

Related U.S. Application Data 2013, now Pat. No. 9,952,165, which is a continuation-in-part of application No. 13/451,019, filed on Apr. 19, 2012, now abandoned.

(51) Int. Cl.
*G01N 23/203* (2006.01)
*G01N 23/223* (2006.01)

(56) References Cited

U.S. PATENT DOCUMENTS

| | | | |
|---|---|---|---|
| 8,494,113 B2* | 7/2013 | Grodzins | G01N 23/223 378/44 |
| 2006/0255265 A1* | 11/2006 | Dalzell | G01N 23/203 250/308 |
| 2007/0058779 A1* | 3/2007 | Yokhin | G01N 23/20091 378/71 |
| 2008/0095309 A1* | 4/2008 | Puusaari | G01N 23/223 378/44 |
| 2009/0116613 A1* | 5/2009 | Kataoka | G01N 23/223 378/47 |
| 2009/0220045 A1* | 9/2009 | Grodzins | G01N 23/223 378/45 |
| 2009/0225944 A1 | 9/2009 | Lee et al. | |
| 2010/0111251 A1* | 5/2010 | Yellepeddi | G01N 23/20 378/44 |
| 2010/0142679 A1* | 6/2010 | Bilderback | G01N 23/203 378/76 |
| 2010/0150307 A1* | 6/2010 | Grodzins | G01N 23/223 378/45 |
| 2011/0007869 A1 | 1/2011 | Gendreau et al. | |
| 2011/0019797 A1 | 1/2011 | Morton | |
| 2013/0279653 A1 | 10/2013 | Hansford | |
| 2013/0321793 A1* | 12/2013 | Hamilton | G01N 23/223 356/72 |

FOREIGN PATENT DOCUMENTS

| | | |
|---|---|---|
| EP | 1650558 A1 | 4/2006 |
| EP | 1672361 A1 | 6/2006 |
| JP | 2000283933 A | 10/2000 |
| JP | 2010038722 | 2/2010 |

OTHER PUBLICATIONS

Dedman, Emma, "International Search Report," prepared for PCT/GB2013/050962, dated Sep. 25, 2013, seven pages.

Mendoza Cuevas, Ariadna, et al., "Portable Energy Dispersive X-Ray Fluorescence and X-Ray Diffraction and Radiography System for Archaeometry," Nuclear Instruments & Methods in Physics Research, Section A: Accelerators, Spectrometers, Detectors, and Associated Equipment, Elsevier B.V., pp. 72-78, Dec. 18, 2010.

Hansford, G.M., "PoDFluX: A new Monte Carlo ray-tracing model for powder diffraction and fluorescence", Review of Scientific Instruments 80, 073903 (2009), 8 pages.

Hansford, G.M., "Back-reflection energy-dispersive X-ray diffraction: a novel diffraction technique with almost complete insensitivity to sample morphology", Journal of Applied Crystallography, Jun. 2011, 44, pp. 514-525.

He, B.B., "Two-Dimensional X-Ray Diffraction", John Wiley & Sons, New Jersey, 2009, pp. 60-63.

Bridges, J.C., et al., "Evaporite mineral assemblages in the nakhlite (martian) meteorites", Earth and Planetary Science Letters 176 (2000), pp. 267-279.

Ebel, Horst, "X-ray Tube Spectra", X-Ray Spectrometry, X-Ray Spectrom, 28, (1999), pp. 255-266.

Kaye & Laby Tables of Physical and Chemical Constants, "4.2.1 X-Ray Absorption Edges, Characteristic X-Ray Lines and Fluorescence Yields," URL: <http://www.kayelaby.npl.co.uk.atomic_and_nuclear_physics/4_2/4_2_1.html>, Retrieved: Oct. 11, 2014, 3 pages.

* cited by examiner

METHODS AND APPARATUS FOR X-RAY DIFFRACTION

This patent application is a continuation application of U.S. patent application Ser. No. 14/394,971, filed on Oct. 16, 2014. U.S. patent application Ser. No. 14/394,971 is a national-stage filing of International Patent Application No. PCT/GB2013/050962, which was filed on Apr. 15, 2013. PCT/GB2013/050962 is a continuation-in-part application of U.S. patent application Ser. No. 13/451,019, filed on Apr. 19, 2012. U.S. patent application Ser. No. 14/394,971, International Patent Application No. PCT/GB2013/050962, and patent application Ser. No. 13/451,019 are incorporated herein by reference.

FIELD

The present invention relates generally to methods and apparatus for X-ray diffraction (XRD).

BACKGROUND

Powder X-ray diffraction (XRD) is a well-known technique for analysis of crystalline materials. Powder XRD methods are usually applied in an angle-dispersive mode (ADXRD). In ADXRD, an X-ray beam with, ideally, a single wavelength $\lambda$ is diffracted by a sample through a range of distinct scattering angles $2\theta$, according to the Bragg equation:

$$\lambda = 2d \sin \theta \qquad (1)$$

The sample is powdered, so that the crystallites within the beam can generally be assumed to be randomly oriented in all directions. The derived set of crystal d-spacings, uniquely characteristic of each mineral phase, is used for phase identification, quantification and structural analysis, amongst other purposes. Energy-dispersive X-ray diffraction (EDXRD) is an alternative application of the Bragg equation. In EDXRD one fixes the scattering angle and scans the X-ray wavelength (equivalently, the X-ray energy). This method can also be implemented without scanning the X-ray wavelength: a broadband X-ray source, such as an X-ray tube, can be used together with an energy-resolving detector.

Both ADXRD and EDXRD have their particular benefits and drawbacks, and find application in different fields. In both techniques, however, X-ray diffraction is sensitive to the morphology of the sample under investigation. As a consequence of this sensitivity, it is difficult to analyse unprepared samples using the conventional techniques. For example, in a geological context, it is difficult to analyse whole rock samples. Rather, a uniform presentation of samples in powder form is required. Therefore the known techniques have limitations on their application, particularly in the field. Samples that are precious and must not be damaged, for example some archaeological artefacts, present difficulties to the powder XRD techniques, for obvious reasons.

SUMMARY

In a first aspect, the invention provides a method of inspecting a material sample by X-ray diffraction wherein the sample is irradiated with a beam of X-ray radiation from a source with a range of photon energies, and wherein a plurality of energy-resolved spectra are obtained from radiation diffracted by the sample, wherein a plurality of energy-resolved spectra are obtained using different settings of source energy, whereby at least one of said spectra excludes a fluorescence signal that is present in another of said spectra.

Said plurality of spectra may be processed together to obtain diffraction information that is substantially independent of fluorescence phenomena over a greater set of energies than can be obtained from any one of the spectra on its own.

In particular, embodiments of the method can use a first one of said spectra to obtain diffraction signals for energies that are obscured by fluorescence signals in a second spectrum, while using information from the second spectrum to obtain diffraction signals for energies that are beyond a range of energies accessible by the photon energy range of the first spectrum. As each energy corresponds in principle to a particular crystal spacing, the additional diffraction information effectively contains information of crystal spacings that would otherwise be unobservable due to the fluorescence phenomena.

The invention provides X-ray diffraction based on energy-dispersive, or wavelength-dispersive XRD. In some embodiments, a diffraction angle of substantially 180° is used. The use of this extreme angle, effectively back-reflection toward the source, helps to make the diffraction spectrum largely insensitive to sample distance or morphology. Therefore useful measurements can be obtained with non-prepared samples such as rocks in their natural form. The use of back-reflection and a fixed angle allows a compact and robust construction of instrument, which may be portable and even hand-held. The instrument can be operated with source and detector closer to the sample than most prior instruments, leading to improved signal strength.

The ability to suppress fluorescence signals using the different spectra is particularly beneficial in the back-reflection applications.

The invention in another aspect provides an apparatus for use in performing energy-dispersive X-ray diffraction to determine characteristics of a material sample, the apparatus comprising:

a source arrangement for irradiating said sample with a beam of radiation at X-ray wavelengths;

a detector for detecting radiation diffracted by the sample; and a processor for resolving the detected radiation into a spectrum of wavelengths, wherein said source arrangement comprises a source of X-ray radiation that is controllable to restrict the maximum photon energy of radiation to different values and to detect and store a plurality of spectra of the same sample with different energy settings, and wherein said processor is further operable to produce a composite diffraction spectrum of said sample, using information from different ones of said plurality of spectra over different sub-ranges of the composite spectrum.

The apparatus may include a controller for automatically controlling said source and said detector to record a plurality of spectra using different maximum photon energies. The apparatus may further comprise a processor for processing said plurality of spectra to obtain from one of said spectra information of diffraction peaks that are obscured by fluorescence signals in another of said spectra.

Again, the ability to record and process spectra at different energy settings is particularly beneficial when performing back-reflection energy-resolved X-ray diffraction. In one embodiment, said source arrangement is located behind said detector, such that said beam of radiation passes beside or through said detector to reach said sample. The detector may substantially or completely surround a path of said beam.

The invention further provides computer program products comprising instructions for causing a processor to perform the controller functions and/or processor functions of an apparatus as set forth above.

In a second aspect, the invention provides a method of inspecting a material sample by X-ray diffraction wherein the sample is irradiated with a beam of X-ray radiation from a source with a range of photon energies, and wherein at least one energy-resolved spectrum is obtained from radiation diffracted substantially back toward the source.

Said energy-resolved spectrum may be processed to obtain information on the spacing of crystal planes in said sample, said information being substantially independent of sample distance or morphology.

The invention in this aspect provides X-ray diffraction based on energy-dispersive or wavelength-dispersive XRD and using a diffraction angle of substantially 180°. The use of this extreme angle, effectively back-reflection toward the source, helps to make the diffraction spectrum largely insensitive to sample distance or morphology. Therefore useful measurements can be obtained with non-prepared samples such as rocks in their natural form. The use of back-reflection and a fixed angle allows a compact and robust construction of instrument, which may be portable and even hand-held. The instrument can be operated with source and detector closer to the sample than most prior instruments, leading to improved signal strength.

In a particular embodiment that combines both the first and second aspects of the invention, plurality of energy-resolved spectra are obtained using different settings of source energy, whereby at least one of said spectra excludes a fluorescence signal that is present in another of said spectra. Said plurality of spectra may be processed together to obtain information on the spacing of crystal planes in the sample over a wider range of spacings than can be obtained from any one of the spectra on its own.

The invention in the second aspect further provides an apparatus for use in performing back-reflection energy-dispersive X-ray diffraction to determine characteristics of a material sample, the apparatus comprising:

a source arrangement for irradiating said sample with a beam of radiation at X-ray wavelengths;

a detector for detecting diffracted radiation returning from a sample in a direction substantially back towards said source; and a processor for resolving the detected radiation into a spectrum of wavelengths.

In one embodiment, said source arrangement is located behind said detector, such that said beam of radiation passes beside or through said detector to reach said sample. The detector may substantially or completely surround a path of said beam.

The source arrangement comprises a source of X-ray radiation may be controllable to restrict the maximum photon energy of radiation to different selected values. This allows diffraction peaks to be identified independently of fluorescence signals that would otherwise obscure them. The apparatus may include a controller for automatically controlling said source and said detector to record a plurality of spectra using different maximum photon energies. The apparatus may further comprise a processor for processing said plurality of spectra to obtain from one of said spectra information of diffraction peaks that are obscured by fluorescence signals in another of said spectra.

In another aspect, the invention provides a method of X-ray diffraction analysis by detecting spectral characteristics of radiation diffracted by a range of angles close to 180°.

The above and other aspects, features and advantages of the invention will be understood by the skilled reader from a consideration of the following detailed description of exemplary embodiments.

BRIEF DESCRIPTION OF THE DRAWINGS

Embodiments of the invention will now be described, by way of example only, with reference to the accompanying schematic drawings in which.

DETAILED DESCRIPTION OF EXEMPLARY EMBODIMENTS

Figure 1:
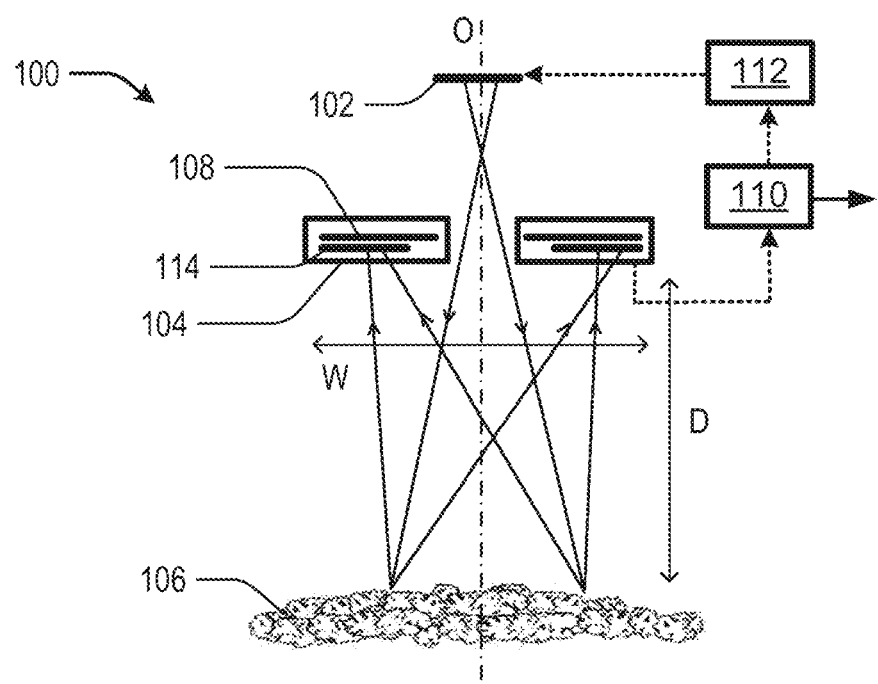
FIG. 1 is a schematic diagram of an apparatus for performing back-reflection energy-dispersive X-ray diffraction (BR-EDXRD) according to an embodiment of the present invention.

We describe herein a method in the field of X-ray diffraction (XRD) which exhibits extremely low sensitivity to the morphology of the sample under investigation. As a consequence of this insensitivity, unprepared samples can be analysed using this method. For example, in a geological context, whole rock samples become amenable to analysis. The fundamental principles of the technique and its experimental validation are explained in detail in an article by the present inventor, namely G. M. Hansford, "Back-Reflection Energy-Dispersive X-Ray Diffraction: A Novel Diffraction Technique with Almost Complete Insensitivity to Sample Morphology", J. Appl. Cryst., 44, 514-525 (2011) [Reference 1]. This paper was first made available to the public on 22 Apr. 2011. Its contents are hereby incorporated by reference.

The back-reflection energy-dispersive XRD produces results in which X-ray fluorescence (XRF) signals can mask XRD signals that are of interest. Further below we describe methods for obtaining XRD spectra in which XRF signals are suppressed. Optionally, a substantially complete XRD spectrum can be synthesized, while suppressing XRF signals.

As mentioned in the introduction, powder XRD methods are usually applied in an angle-dispersive mode, whereby an X-ray beam with, ideally, a single wavelength λ is diffracted through a range of distinct scattering angles 2θ according to the Bragg equation:

$$\lambda = 2d \sin \theta \quad (1)$$

For a microcrystalline sample, peaks in the intensity of diffracted radiation are observed at specific angles, each corresponding to a different spacing d of planes in the crystal structure. The derived set of crystal d-spacings, uniquely characteristic of each mineral phase, is used for phase identification, quantification and structural analysis, amongst other purposes. In energy-dispersive X-ray diffraction (EDXRD), which is the basis of the present invention, one fixes the scattering angle and scans the X-ray wavelength (equivalently, the X-ray energy). This method can also be implemented without scanning the X-ray wavelength: a broadband X-ray source, such as an X-ray tube, can be used together with an energy-resolving detector. In either case, peaks in the intensity of diffracted radiation are observed at specific energy (wavelength) values in the spectrum of energies detected by the detector. Energy in this context refers to the photon energy (corresponding to the frequency or wavelength of the radiation), rather than the intensity of radiation at the specific energy that can be measured in terms of photon count. Again, each peak corresponds to a different spacing d of planes in the crystal.

The novel technique described here applies energy-dispersive X-ray diffraction (EDXRD) in a back-reflection geometry, i.e. with 2θ close to 180°. An insensitivity to the sample morphology follows in part from this geometry. Three key characteristics of the method and apparatus for performing the novel technique are:

1. Detection of X-ray photons diffracted by the sample such that the 2θ diffraction angles of the detected photons are all close to 180°. The acceptable range of angles depends on the details of the implementation. The method does not require measurement or knowledge of the specific angles of the detected photons.

2. Resolution of the energies (or wavelengths) of the diffracted photons, or knowledge of their energies by some means. This could be achieved with an energy-dispersive detector, such as a silicon drift detector, or any type of X-ray spectrometer such as a wavelength-dispersive spectrometer.

3. The diffraction angle is substantially fixed. Therefore in order to access a range of crystal d-spacings, the X-ray source should either be a broadband source or a source which can be scanned through a range of energies. Suitable sources include, but are not limited to, X-ray tubes and synchrotron sources.

Where the source can be scanned through a range of energies, in principle the detected energy (wavelength) might be implicitly resolved, without an energy-resolving detector. In practice the energy-resolving detector is nonetheless useful.

FIG. 1 shows one exemplary apparatus 100 for use as an instrument performing back-reflection energy-dispersive XRD. The instrument 100 includes an X-ray source 102, and a detector assembly 104 facing a sample 106 positioned at a distance D from the detector assembly. The instrument in this example further include a controller 110 and a source driver 112. The source 102 is configured to apply an X-ray beam onto sample 106 with a range of angles, dictated by a collimator 108. Detector assembly 104 is largely circularly symmetric, so that the collimator is an annular shield of metal or other material suitable for blocking the X-rays, except in a central aperture lying on an optical axis O.

Also within detector assembly 104 is an energy dispersive detector 114 which may also have an annular form, so as to detect radiation diffracted back from the sample. Specifically, radiation is detected with a range of diffraction angles 2θ that lie close to 180°, within limits set by the geometry of the source, the collimator, the detector and the sample. Note that diffracted radiation returning at exactly 180° are not generally detected because they return through the aperture in the detector and toward the source. The diffracted radiation detected by the detector may have a diffraction angle greater than 155°, for example, or greater than 160°.

It is understood that FIG. 1 shows just one possible configuration of the source, the sample and the detector, while quite different arrangements are possible. For example, the X-ray source 102 may also be co-planar with the detector 114, or it may lie in front of the detector. The collimator and detector do not need to be within the same assembly 104. Use of an annular detector is not essential, but is advantageous in order to collect most or all of the complete Debye-Scherrer diffraction rings. The detector 114 can instead be a conventional detector mounted to one side of the X-ray source, or a number of separate detectors arrayed around the axis O. Other configurations are possible, such as an annular source with a central aperture, behind which sits a detector (i.e. inverting the roles of the source 102 and detector 114 in FIG. 1). Some of these configurations may be difficult to achieve in practice because of the need to accommodate the X-ray source and the detector in relatively close proximity.

For certain applications it may be desirable to control the width of the X-ray beam footprint on the sample. For example, the user may wish to analyse a restricted portion of the sample. In other cases, a large footprint may be desirable in order to ensure that a sufficient number of crystallites are illuminated so that the crystallite orientations are effectively randomized. The illumination width could be controlled with a variable-aperture collimator 108, or by changing the distance between the instrument and sample (within limits set by the angular requirements).

In all cases, the design is made such that: the geometrical configuration of the source, sample and detector restricts the detected radiation to that with 2θ close to 180°. Some tolerance either side of 180° is available, however, because around 2θ=180° the function sine in the Bragg equation is only slowly varying with θ.

Use of currently available energy-dispersive detectors gives limited energy resolution, although future technological developments may improve on currently available detectors. Higher spectral resolution can be achieved through the use of an X-ray monochromator (not shown) positioned either between the source 102 and the sample 106, or between the sample 106 and the detector 114. In the latter position, such an arrangement would conventionally be called an X-ray spectrometer. Many different designs of X-ray monochromators and spectrometers are possible. However, the arrangement should satisfy the three characteristics listed above, in order to achieve insensitivity to the sample morphology.

By ensuring a minimum distance (D>=$D_{min}$) between the sample 106 and the detector 114, only those photons which diffract at angles close to 180° are registered by the detector. Since each photon travels back along its incident path (approximately), the distance between the detector and the interaction point on the sample becomes irrelevant. By extension of this argument, it is also irrelevant if different parts of the sample lie at different distances to the detector. As described in the article of reference 1, detailed analysis and ray-trace modelling shows that, for an angular range limited to 2θ≈160° to 180°, dependent on the details of the implementation, the technique retains quite remarkable insensitivity to sample morphology. This insensitivity has also been demonstrated in proof-of-principle experiments, which will be illustrated further below with reference to FIG. 2.

In summary, therefore, a method of inspection of a sample comprises irradiating the sample with X-rays from a source position at a range of wavelengths, and detecting peaks in a spectrum of radiation diffracted by the sample in a direction substantially opposite to the direction of irradiation. By using only those photons which have been diffracted through angles close to 180°, together with detection of the energy of the photons, the novel technique can reveal crystal structure with insensitivity to sample morphology. For any given instrument configuration, the range of angles can be restricted within a desired range around 180° by ensuring a certain minimum distance between the sample 106 (more precisely, the nearest point on the sample) and the part of the instrument nearest to the sample (X-ray source 102 and/or the detector 114). The required minimum distance depends on the details of implementation and the desired energy resolution, as described in Reference 1 mentioned above. If this minimum distance is not achieved, then the diffraction peaks in the measured spectrum will be unduly broadened. For reasons explained in more detail in Reference 1, the extent of such 'geometric broadening' is only weakly dependent on the divergence (angular spread) of the primary beam. For a configuration such as the one shown in FIG. 1, the minimum distance $D_{min}$ can most usefully be expressed as a minimum ratio of the sample-detector distance D to width or diameter W of (an active area of) detector 114. The ratio D:W may be for example as small as 1.1, though larger ratios such as 1.33, as in the geometry described in Reference 1, or even greater may be preferred. This ratio serves to ensure that the spectral resolution is limited by the detector (for a silicon drift detector) rather than by geometric broadening. For the same instrument configuration, a substantially larger ratio would make a negligible difference to the spectral resolution but would give substantially lower count rates at the detector. Thus, in this type of instrument configuration and using commonly-available detectors, a distance D of approximately 20 mm is optimum. The distance between the sample and detector(s) in conventional angle-dispersive XRD instruments is normally markedly greater, often more than 100 mm.

As the strength of diffraction signals falls with the square of the distance D, the fact that the detector can be positioned closer to the sample than in most prior instruments allows greater signal strength for a given source power, or reduced source power for the same signal strength. The distance to the source may be less than 100 mm, less than 70 mm or less than 50 mm.

For an instrument configuration designed to achieve significantly higher spectral resolution than obtainable with a silicon drift detector as the only energy-dispersive element, the range of angles close to 180° should be more restricted in order to reduce geometric broadening. For example, if the X-ray source in FIG. 1 is replaced with a combined source and X-ray monochromator, mounted behind the same detector, then the sample-detector distance D must be increased so that the angular range is smaller. Geometric broadening can be substantially reduced even for relatively modest increases in the distance D. For example, if D is increased from 20 mm to 30 mm, the achievable spectral resolution is markedly improved, assuming suitable monochromator resolution. The appropriate value of D can be calculated using the method outlined in Reference 1. Whatever the instrument design, increasing the distance to the sample will reduce the range of angles closer and closer to 180°, and will reduce the geometric broadening.

Experiments

Some experiments have been conducted to demonstrate feasibility of the novel method, and in particular to confirm that it is insensitive to sample morphology. These have been performed using an experimental apparatus modelling the apparatus of FIG. 1. A CCD detector was used that is position-sensitive, as well as energy-dispersive, but the position information was not used except to delimit a region-of-interest on the CCD. This allowed experimentation with the angular restriction requirement of the back-reflection EDXRD method. A light-blocking filter comprising a 15 μm thick foil of aluminium was used to prevent light from the X-ray tube filament from reaching the CCD which is sensitive to visible light as well as the desired X-ray wavelengths. Such a filter, not shown in FIG. 1, can be used if necessary in a practical instrument, depending on the type of detector. This filter heavily attenuates X-rays in the range 1.56 keV (the Al—K absorption edge) to ~3 keV, and so diffraction peaks in this range have very low intensity.

Depending on the details, this filter can be much thinner or eliminated altogether in alternative configurations. Thinner filters do not attenuate the wanted X-ray radiation so much, but typically are more expensive and/or fragile. Filters can be integrated with a source housing or a detector or detector housings, rather than provided separately.

Figure 2:
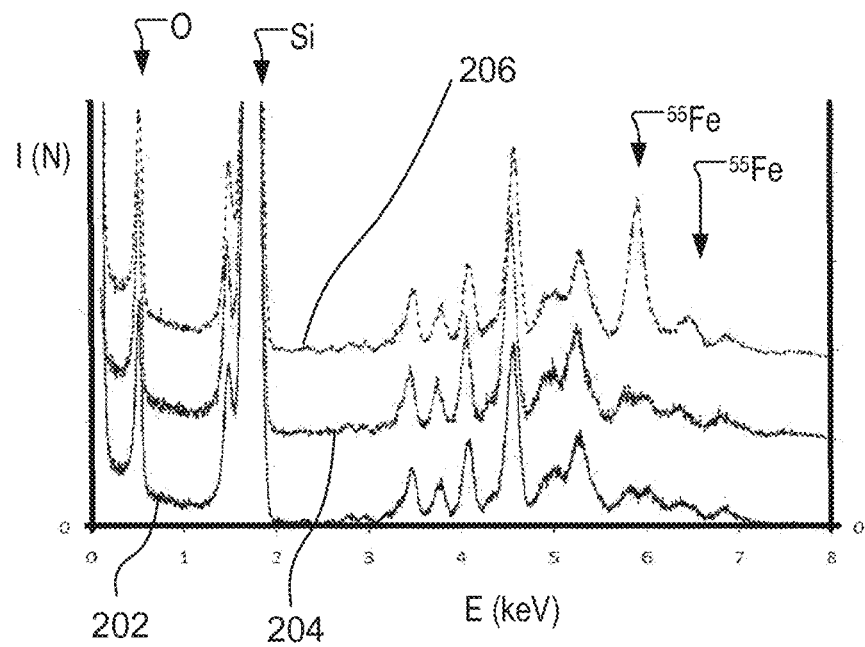
FIG. 2 illustrates back-reflection EDXRD spectra of a conventional powder sample in three different positions.

FIG. 2 shows the intensity spectra 202, 204 and 206 obtained using a pressed-powder pellet of quartz mounted at three different positions and orientations. This type of sample is prepared in the conventional manner for powder XRD. The sample positions for each trace are:

202: a nominal position about 70 mm from the detector (202),

204: a position 28 mm further away from the X-ray source, and

206: the nominal position but rotated away from the detector by 45°.

Figure 3:
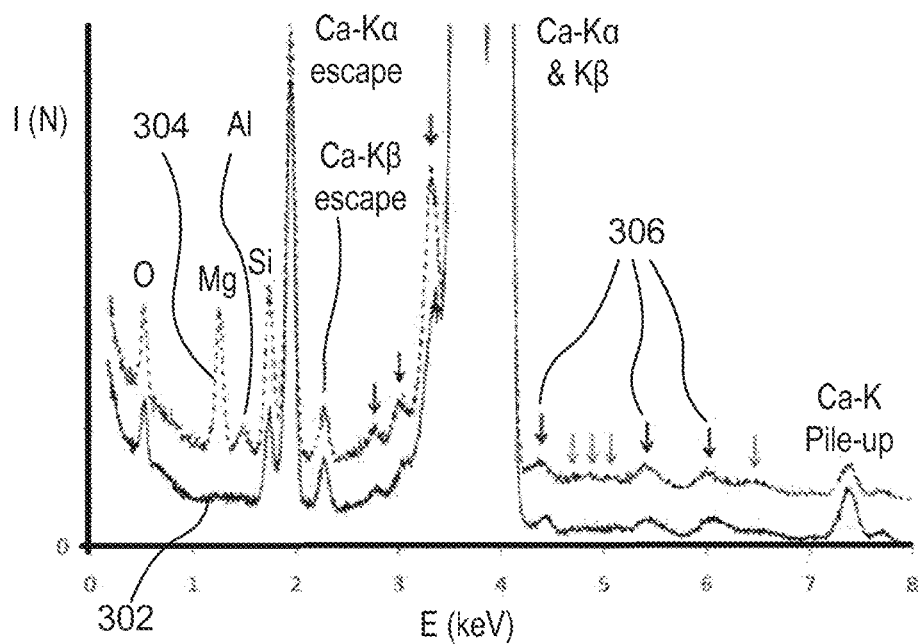
FIG. 3 illustrates a back-reflection EDXRD spectrum of a conventional pressed-powder sample compared to the spectrum of a whole rock sample.

In FIG. 2, the Si and O fluorescence peaks are labelled as are two peaks due to the inadvertent exposure of an $^{55}$Fe calibration source. All other peaks are due to diffraction from quartz. The three graphs have been offset on the vertical scale for clarity. The graph for 28 mm displacement of the sample (spectrum 202) is plotted on a magnified intensity scale, for ease of comparison. It will be seen that the three graphs in FIG. 2 show a very high degree of correspondence, after allowing for the reduced intensity when the sample was positioned further from the source. It should be emphasized that these experimental changes of position and orientation represent movements of the sample of a size which conventional XRD methods would be completely unable to cope with. Even diffractometry methods which are designed to allow some degree of sample morphology and surface roughness cannot accommodate sample movement of this magnitude. Such a method is the parallel-beam diffractometry described by B. B. He, in "Two-Dimensional X-Ray Diffraction", John Wiley & Sons, New jersey (2009) [Reference 3], FIG. 3 illustrates another experiment that confirms that the analysis of a whole rock specimen is feasible, that is without preparation of a special powder sample. A piece of limestone, chosen for its simple mineralogy, was mounted in a test chamber with the experimental apparatus described above with reference to FIG. 2. This sample of limestone consists mainly of calcite, $CaCO_3$, with minor amounts of dolomite, $CaMg(CO_3)_2$. The rock was not positioned at a precisely-known distance from the source, and indeed its irregular surface would defeat any attempt to do so. The spectrum of the limestone was compared with the spectrum of a pressed-powder pellet of calcite, that is to say with a sample prepared as for conventional XRD.

In FIG. 3, solid trace 302 shows the back-reflection EDXRD spectrum of the calcite pressed-powder sample while solid trace 304 is the spectrum of a whole rock limestone sample (dotted trace 304). The traces 302, 304 in FIG. 3 have been offset on the vertical scale for clarity. The fluorescence and associated peaks of various elements are labelled with their chemical symbols, while the diffraction peaks are marked with arrows 306. Comparing the two traces, one can see some minor differences, notably the presence of a Mg fluorescence peak in the limestone data, indicative of dolomite. However, one can also see that the diffraction peaks seen in the prepared calcite spectrum are reproduced in the limestone rock spectrum. This sample would benefit significantly from the suppression of the Ca—K fluorescence peaks by the method described herein. The peaks marked as 'escape' peaks are detector artefacts associated with the Ca—K fluorescence peaks, and these would also be suppressed.

Suppression of X-Ray Fluorescence Peaks

In addition to the X-ray diffraction, the irradiation with X-rays can give rise to X-ray fluorescence (XRF) in many samples. In these cases, XRF peaks will appear in the detected X-ray spectrum alongside peaks clue to diffraction. The XRF peaks yield information about the elemental composition of the sample, and this information can be used to complement the information derived from X-ray diffraction.

While the presence of XRF peaks in the detected spectrum may in some instances be beneficial to the analysis of the sample, these peaks tend to be considerably more intense than the diffraction peaks, and may overlay and obscure them. In these cases, the presence of XRF peaks is likely to be detrimental to the analysis of the sample. Measures for selectively suppressing the XRF peaks in order to reveal hidden diffraction peaks are presented below. It is found that the energy of the XRF peak(s) for any given element is characteristic of that element, and this can help to distinguish XRF and XRD peaks. Therefore signals both with and without XRF suppression will be useful in general, and can be used together in analysing a sample of unknown material.

In conventional, angle-dispersive XRD, XRF from the sample contributes to the background signal, rather than producing peaks which may be confused with diffraction peaks. There are methods for suppressing the fluorescence signal in conventional XRD, but these are distinct from the method described herein.

To demonstrate the suppression of XRF peaks, some simulations have been performed. These simulations use the well-validated ray-trace Monte Carlo model PoDFluX, as described in an article Graeme M. Hansford, "PoDFluX: a new Monte Carlo ray-tracing model for powder diffraction and fluorescence", Rev. Sci. Instrum., 80, 073903 (2009) [Reference 2]. The 'sample' for these simulations consists of the mineral Jarosite, which has the chemical formula $KFe_3(SO_4)_2(OH)_6$. Note that the same method can be applied to samples consisting of other minerals or mixture of minerals (or, more generally, crystalline substances). Further examples of Limestone, Lafayette and Basalt will be illustrated below. All of the simulation results presented here are for experiments performed in a back-reflection geometry, for 2θ close to 180°. The same procedure can be followed for EDXRD experiments at other 2θ scattering angles. The invention is not limited to application in back-reflection EDXRD.

Figure 4:
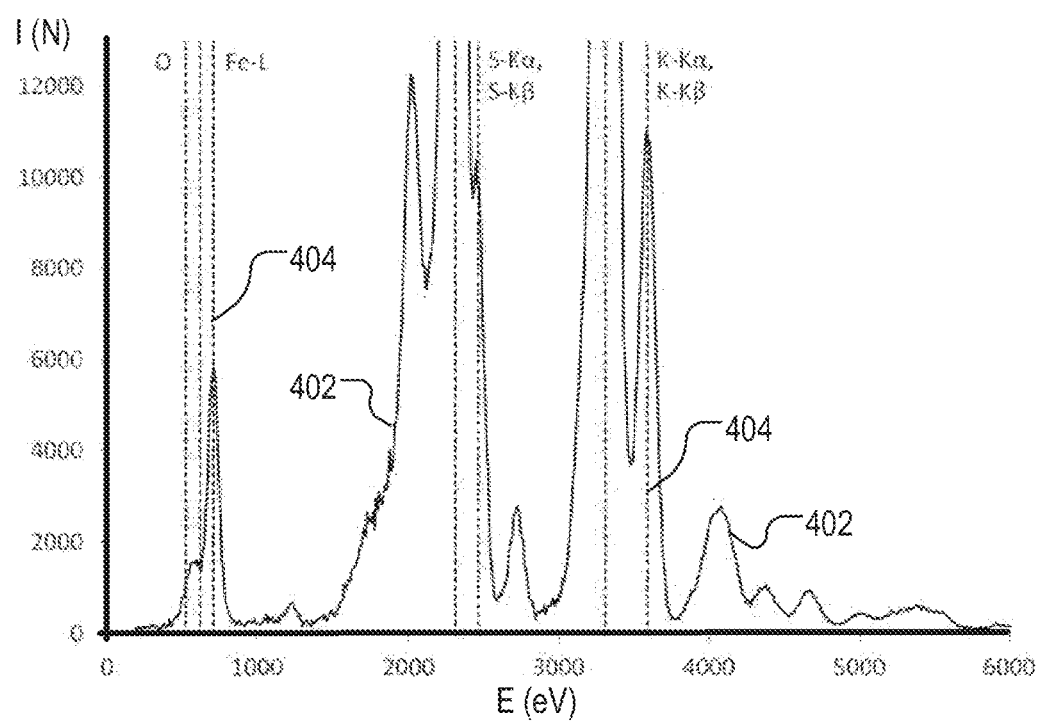
FIG. 4 illustrates a simulation of the spectrum of a Jarosite mineral sample in a first method employing the apparatus of FIG. 1.

FIG. 4 illustrates in trace 402 a simulation of the detected spectrum of a Jarosite sample for an instrument configured as shown in FIG. 1, with a tube excitation voltage of 7.1 kV and a current of 0.2 mA, and for a data acquisition period of one minute. Suitable X-ray tubes are readily available. In FIG. 4, the vertical axis is scaled to emphasize the diffraction peaks, with the result that some of the XRF peaks, marked with dotted lines 404 etc., are off-scale. The XRF peaks are marked with dotted vertical lines, all other peaks in the spectrum are due to diffraction. The strength of the S—Kα, S—Kβ, K—Kα, and K—Kβ peaks means it is not possible to determine whether there are diffraction peaks lying at the same or similar X-ray energies.

In order to understand how the method of fluorescence suppression described here works, it is important to have some basic knowledge of the properties of X-ray tube sources. The range of photon energies (wavelengths) emitted by an X-ray tube type of source is limited by the voltage at which the tube is energized. For example, if the X-ray tube excitation voltage is set to 7.0 kV, none of the photons emitted by the tube will have an energy above 7.0 keV. The X-ray source will emit Bremsstrahlung photons in a continuous spectrum with energies up to 7.0 keV. X-ray tubes also emit X-rays corresponding to the characteristic lines of the element(s) comprising the anode, though these are not of interest for the purposes of energy-dispersive XRD. X-ray tubes are often used with a window (commonly made of Be) which will limit the flux of low energy photons, below 1.0 key for example. The combination of the excitation voltage, the anode material, and the window together determine the energy spectrum of X-rays emitted by the source. The total X-ray flux of an X-ray tube source is also determined by the emission current. An increase in the emission current at the same excitation voltage gives rise to a proportionate increase in the X-ray flux, without changing the energy spectrum. Greater signal levels in the detected spectrum can be achieved by, for example, increasing the tube emission current or extending the acquisition period. All of the simulations reported below use the instrument geometry described in Reference 1, an acquisition period of one minute, and a tube emission current of 0.5 mA, unless otherwise noted.

The ability to restrict the maximum photon energy in the source radiation can be used as the basis of a method to suppress XRF peaks and allow better detection of XRD phenomena. As an example, we consider the sulphur, S, and potassium, K, XRF peaks in the spectrum of Jarosite. Taking the example of potassium, the K$\alpha$, and K$\beta$ peaks occur at the energies 3313 and 3590 eV respectively. However, these fluorescence peaks are only excited if there are X-ray photons incident on the sample with energies greater than 3607 eV, the K-edge absorption energy of potassium. If the X-ray tube excitation voltage is set just below this, say to 3.6 kV, none of the photons incident on the sample can have sufficient energy to excite K fluorescence. The X-ray source will emit. Bremsstrahlung photons with energies up to 3.6 key, and so diffraction peaks which would otherwise be obscured by the K fluorescence will nevertheless appear in the spectrum. This assertion is demonstrated by the simulations shown in FIG. 5a. The application of these observations in a practical method will be described further with reference to FIG. 6. If an X-ray source other than an X-ray tube is used, for example a synchrotron, the maximum energy of the X-ray photons from the source may be restricted in some other way.

Figure 5A:
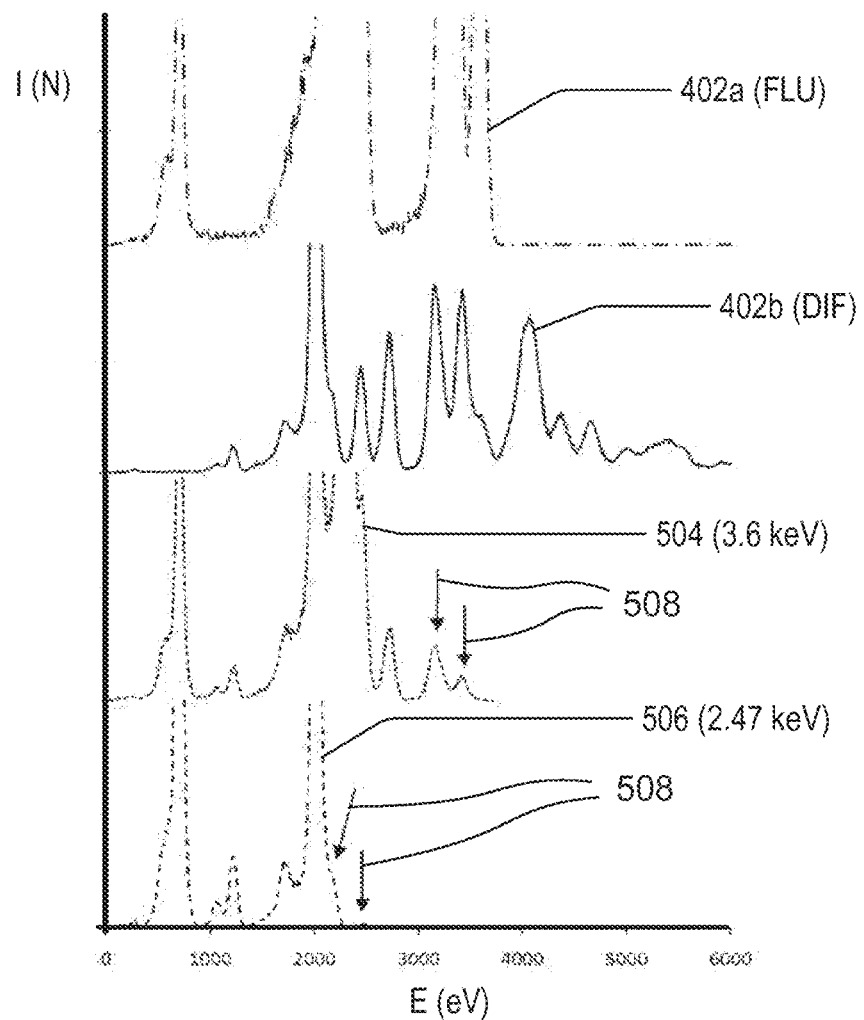
FIG. 5a illustrates simulated spectra of the Jarosite mineral sample in a second method employing the apparatus of FIG. 1, illustrating the principle of suppression of X-ray fluorescence signals in accordance with an embodiment of the present invention.

FIG. 5a shows several PoDFluX simulations of spectra of a Jarosite sample for an instrument configured as described in reference 1 and operated with the source energized to different voltage levels. In FIG. 5a, spectra have been offset on the vertical axis for clarity, and have had intensity normalization factors applied for ease of comparison. All of the simulations use moderate emission currents in the range 0.2 to 1.0 mA, and each spectrum represents data acquisition for a period of one minute.

The top part of FIG. 5a shows the intensity, I, detected for a tube excitation voltage of 7.1 kV. As far as the detector is concerned, the measured spectrum would be the same as trace 402 in FIG. 4, but for this illustration the simulated contributions 402a of fluorescence (FLU) and 402b of diffraction (DIF) are plotted separately in order to highlight their contributions to the spectrum in FIG. 4. The trace 504 of FIG. 5a shows the simulated spectrum that would be detected from the same sample for a tube excitation voltage restricted to 3.6 kV, causing the suppression of the K fluorescence. The lower trace 506 of FIG. 5a shows the simulated detected spectrum for a tube excitation voltage restricted to 2.47 kV, causing the suppression of both K and S fluorescence. The arrows 508 in FIG. 5a indicate diffraction peaks which are revealed by suppression of K and S fluorescence by tuning the X-ray tube excitation voltage below the excitation energies.

Figure 5B:
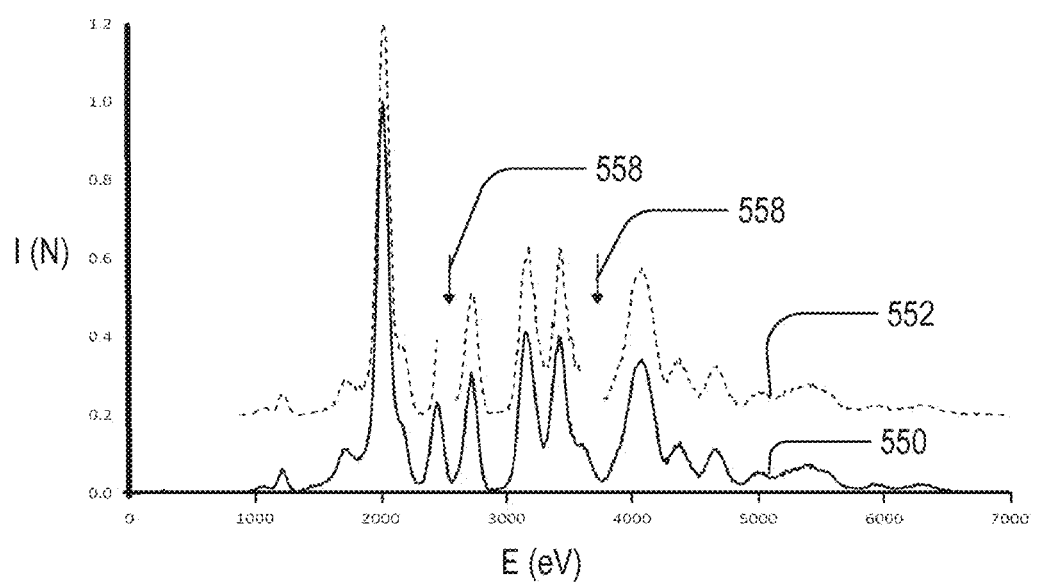
FIG. 5b shows a diffraction-only simulation of the back-reflection EDXRD spectrum of the Jarosite sample for a tube excitation voltage of 7.1 kV, compared to a reconstructed diffraction pattern.

FIG. 5b shows a diffraction-only simulation of the back-reflection EDXRD spectrum of the Jarosite sample for a tube excitation voltage of 7.1 kV, compared to a 'reconstructed' diffraction pattern. In the present invention, the analysis on the obtained spectra may be taken further by reconstructing the diffraction pattern which would be observed in the absence of any fluorescence. As an example, the results of this process for a tube excitation of 7.1 kV are shown in FIG. 5b in which the lower trace 550 of a diffraction-only simulation is compared with a top trace 552 of a reconstructed diffraction pattern. The reconstructed pattern can consist of three parts which include the spectrum above 3.8 keV taken directly from a first simulation, the spectrum in the range of 2.6 to 3.6 keV taken from the simulation for K suppression, and the spectrum in the range 0.9 to 2.45 keV taken from the simulation for K and S fluorescence suppression. The spectrum is scaled in intensity according to the difference in the excitation conditions of the X-ray tube, in order to reproduce the expected relative peak intensities for a tube excitation voltage of 7.1 kV. The arrows 558 in FIG. 5b indicate gaps in the reconstructed diffraction pattern.

Another way to minimize overlap of XRF and XRD signals is to use a more energy-selective detection and/or irradiation arrangement. As already mentioned, tunable monochromators are available which allow very narrow bands of wavelengths to be selected.

Methods & Applications

The instrument of FIG. 1 can be provided in any suitable form. The fixed back-reflection geometry permits a particularly compact and robust construction, and may be particularly suited for implementation as a portable, even hand-held device. In this way, the instrument can be presented to samples where they lie, be that in the ground, in a museum. It may be mounted on a probe for exploration of an extra-terrestrial body. Further discussion of such application is contained in Reference 1.

Figure 6:
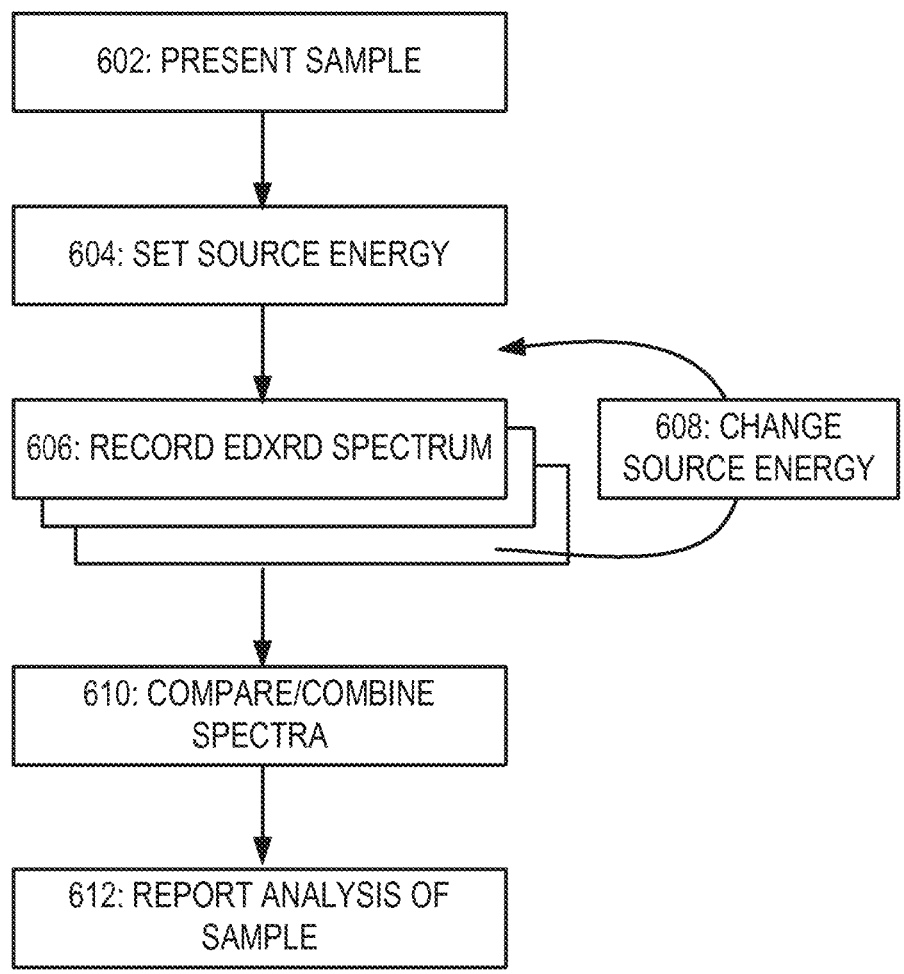
FIG. 6 is a flowchart of a method employing the apparatus of FIG. 1 and including steps for suppressing X-ray fluorescence signals.

FIG. 6 is a flowchart illustrating the main steps in a measurement technique using the principles described above. Operation of the apparatus and analysis of the results can be automated as desired, by computer programming, for example by programming a computer within controller 110. A method which includes the suppression of XRF signals is illustrated by the flowchart of FIG. 6.

In FIG. 6, step 602 involves presenting the sample to the instrument at a distance that is not critical, but is greater than or equal to a prescribed minimum distance ($D>=D_{min}$). At 604 a value of the source energy is set within the source driver 112, either manually or under computer control. At 606 a spectrum of the back-reflected radiation (i.e. radiation diffracted with angle 180° or so) is recorded from the sample. As explained with reference to FIG. 5a, there can be advantages in setting a lower energy, to avoid exciting certain fluorescence peaks. On the other hand, a higher energy (shorter wavelength) may be required to see certain diffraction peaks (certain crystal spacings d). Therefore, at 608 the source energy is increased or decreased to a new setting, and step 606 repeated to record another spectrum. The steps 608 and 606 are repeated until a full desired set of spectra have been recorded.

The settings may be numerous or few. They may be the same for all samples, or they may be selected in accordance with the fluorescence characteristics of materials anticipated to be in the sample. The energy settings may alternatively or in addition be selected adaptively, based on fluorescence peaks observed in the first recorded spectra. For example the first setting may be a maximum energy, such as 7.1 keV and reduced energy settings such as 3.6 keV and 2.47 keV may be selected based on fluorescence peaks observed in the first recorded spectrum. The selection of energy settings may be by manual control, or may be automated.

At 610 the spectra are compared and combined to obtain a full set of diffraction peaks, from which fluorescence signals have been suppressed as much as possible. In a simple implementation, the spectrum for the lowest energy setting is used as the authoritative for energies up to the maximum energy recorded in that spectrum, then the next lowest and so forth. More sophisticated combinations may be designed, for example to substitute values from one spectrum or another specifically in the region of known or expected fluorescence peaks.

At 612, some analysis of the diffraction signals is performed, optionally informed by information from other sources. In a direct implementation, the set of crystal plane distances d is reported based on the energies (wavelengths) of the detected peaks, and optionally on the relative intensity of radiation (photon count) in each peak. Other methods to identify and/or quantify the crystalline phases present in the sample may be used, such as comparison with a set of standardized spectra from reference samples, or by comparison with model simulations. These methods may be especially useful in cases where the individual crystal plane spacings give rise to diffraction peaks which cannot be separately resolved, using the chosen detection system, geometry etc. In other words, peaks need not be identified individually in the spectrum, but may be contributing to an overall spectral profile which depends on a combination of the crystal plane spacings, the energy resolving performance of the detection system, the geometry of the source and detector relative to the sample and other factors. These factors can be taken into account in providing a library of model spectra. The absence of a peak may be just as significant as the presence of a peak, when considered in the context of the spectrum as a whole and/or information from other sources.

Reconstruction of Diffraction Spectra—Example Limestone

Figure 7:
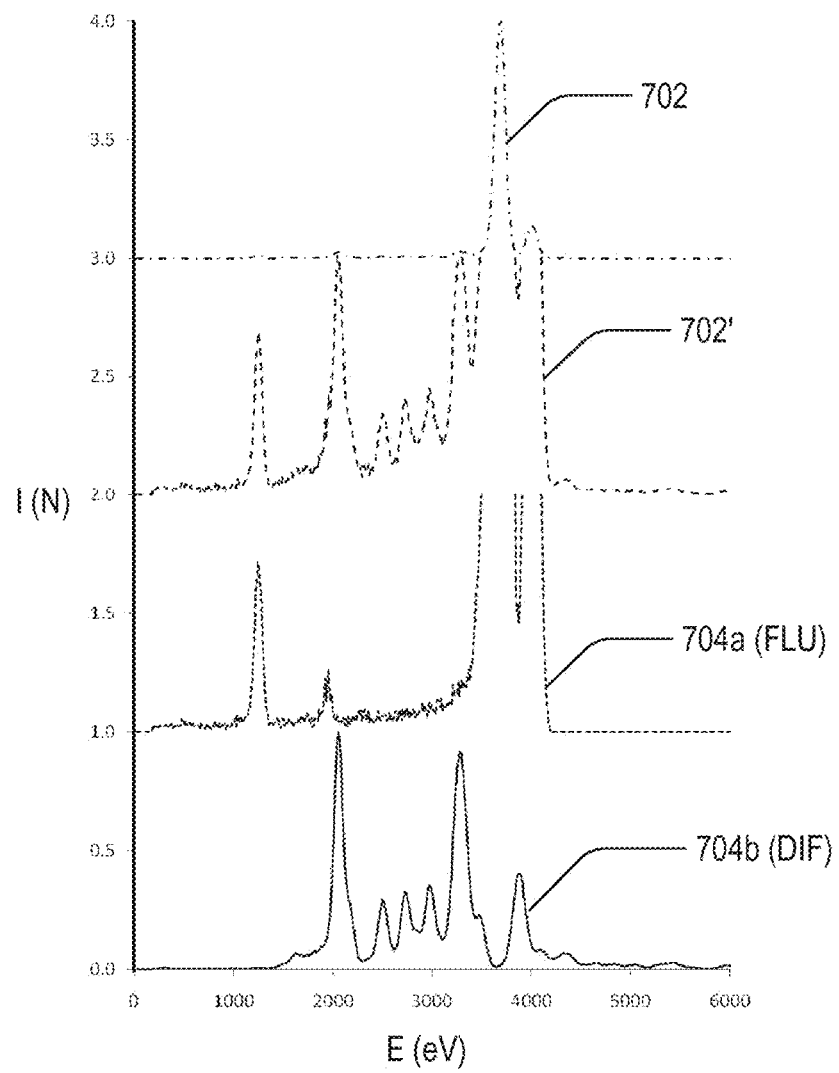
FIG. 7 shows simulations of the back-reflection EDXRD spectra of a limestone sample, for a tube excitation voltage of 7.0 kV.

FIG. 7 shows simulations of the back-reflection EDXRD spectra of a limestone sample. The sample is intended to represent a limestone rock, and consists of 80% calcite, $CaCO_3$, and 20% dolomite, $CaMg(CO_3)_2$ (all mineral proportions are specified as % by volume unless otherwise stated). FIG. 7 shows the simulations 702, 702' of the detected spectrum, alongside simulations 704a and 704b which include the fluorescence process only, and the diffraction process only, in the same manner as FIG. 5a. The latter two simulations are included to illustrate the problem of fluorescence peaks obscuring diffraction peaks, but cannot be directly observed by a real instrument. The spectra 702', 704a and 704b have been normalized to the same vertical scale, while the top-most trace 702 has been normalized (scaled down) to show the strong Ca—K fluorescence peaks.

The X-ray tube source for these simulations was set to an excitation voltage of 7.0 kV. There are very strong Ca—K fluorescence peaks which obscure the diffraction peaks in the energy range 3.4 to 4.2 keV. In addition, there is an Mg—K fluorescence peak at ~1.25 keV which lies at lower energy than any of the diffraction peaks. The remaining peak at ~1.85 keV in the 'fluorescence-only' spectrum is an 'escape' peak—a detector artefact associated with the strong Ca—Kα peak at 3.69 keV (Reference 4 is a database of absorption and fluorescence peaks & edges). The strength of this peak relative to the Ca—Kα fluorescence peak depends on the details of the detector and signal conditioning electronics, but the simulation is representative of the intensity observed in laboratory data. C and O also have fluorescence peaks, but they are extremely weak and occur below 0.6 keV.

Figure 8:
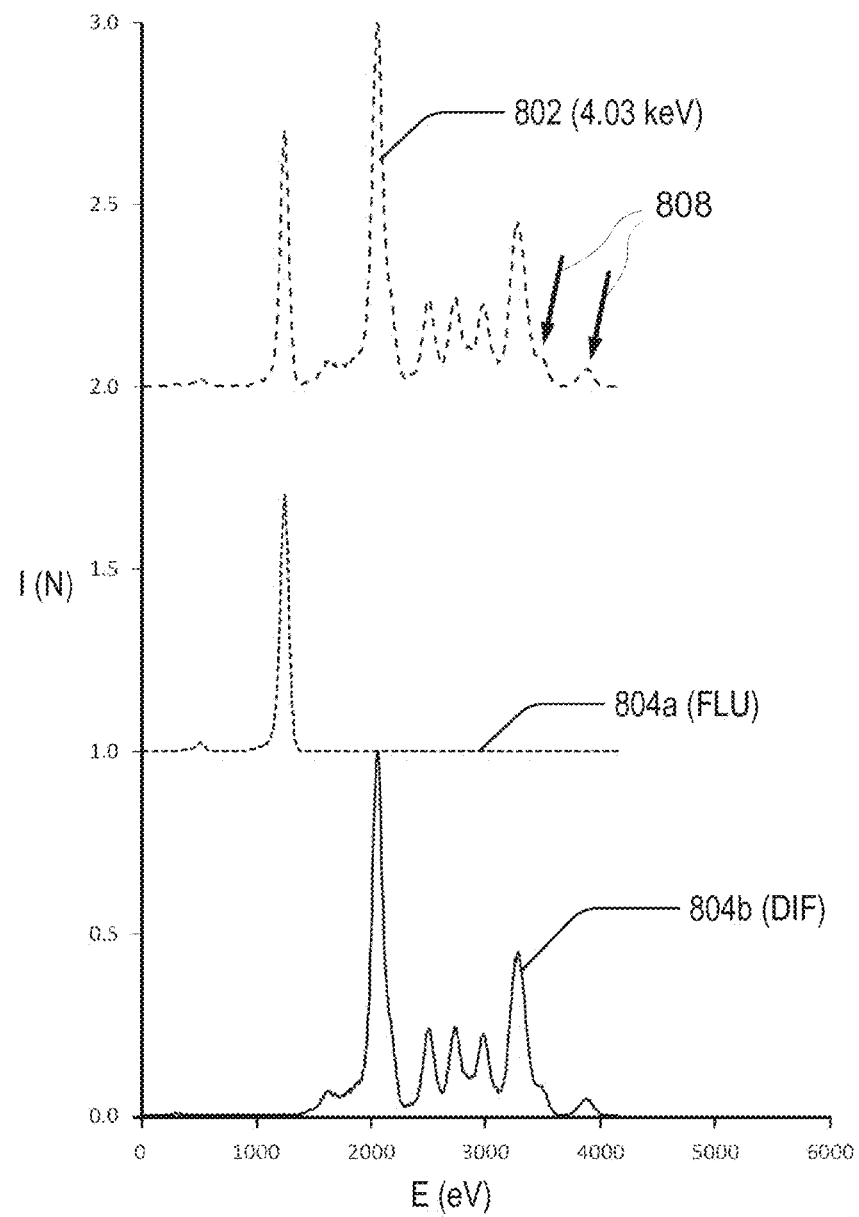
FIG. 8 shows simulations of the back-reflection EDXRD spectra of the limestone sample, for a tube excitation voltage of 4.03 kV.

Fluorescence from Ca in the sample is only stimulated by X-rays incident on the sample with energies greater than the Ca—K absorption edge energy which is at 4.034 keV. Operating the X-ray tube at an excitation voltage below this energy will ensure that no X-ray photons incident on the sample will be able to stimulate Ca fluorescence. FIG. 8 shows simulated traces 802, 804a, 804b substantially similar as for FIG. 7, except with a tube excitation voltage of 4.03 kV. The Ca—K fluorescence peaks and the Ca—Kα escape peak are all now absent in the spectrum. The diffraction peaks which were obscured when operating at 7.0 keV are indicated with arrows 808 in FIG. 8.

Figure 9:
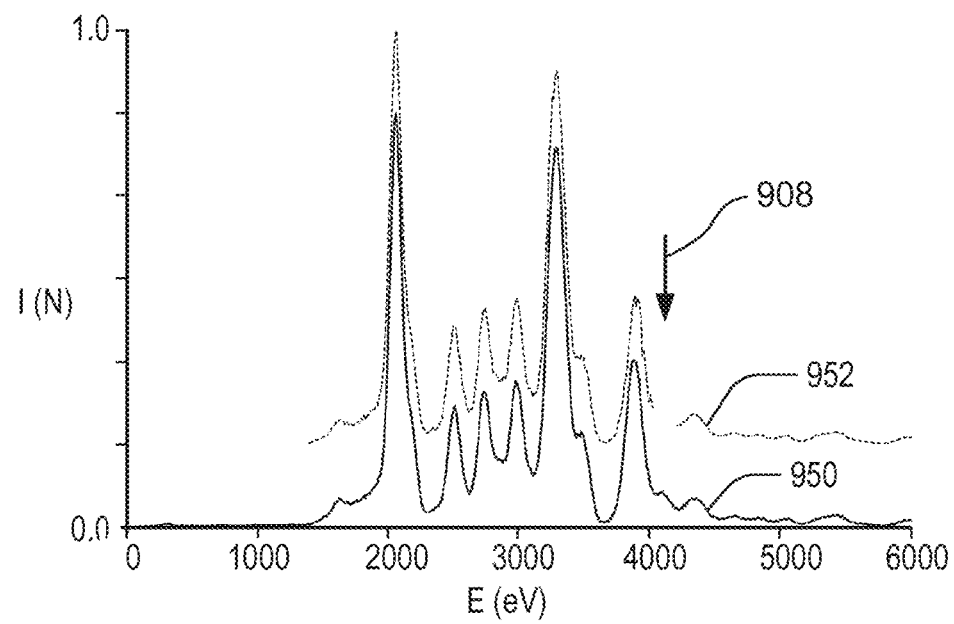
FIG. 9 shows simulations of the back-reflection EDXRD spectra of the limestone sample, for a tube excitation voltage of 7.0 kV (lower trace), and a reconstructed diffraction pattern (upper trace) produced by a method according to an embodiment of the invention.

As explained already with reference to FIG. 5b, the analysis can be taken further by synthesizing or 'reconstructing' the diffraction pattern which would be observed in the absence of any fluorescence over a wider full spectral range than is provided by either measurement alone. The results of this process are shown in FIG. 9 in which the original (7.0 keV excitation) 'diffraction-only' simulation 950 is compared with a reconstructed diffraction pattern 952. The reconstructed pattern consists of two parts. Firstly, the spectrum above 4.2 keV is taken directly from the first (simulated) measurement. Secondly, the spectrum in the range 1.4 to 4.0 keV is taken from the second measurement, suppressing Ca—K fluorescence.

Figure 10:
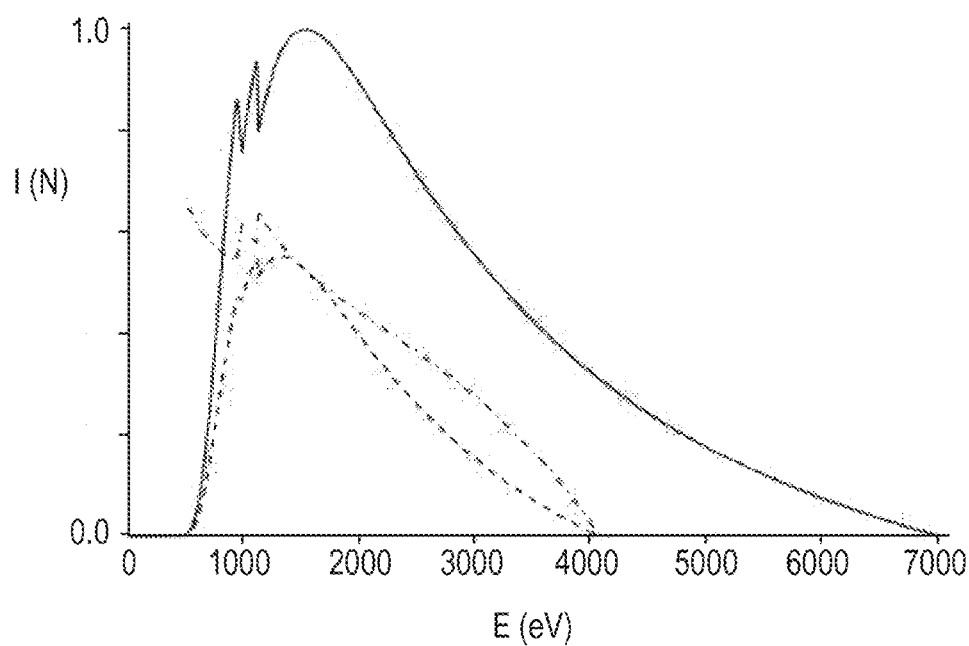
FIG. 10 shows calculated normalized Bremsstrahlung X-ray intensity output for tube excitation voltages of (a) 7.0 kV and (b) 4.03 kV, both with a copper anode and after transmission through an 8 μm Be window, and (c) the ratio of the latter to the former.

To produce the synthesized spectrum, the partial spectra are scaled in intensity relative to one another according to the difference in the excitation conditions of the X-ray tube. In the example, the spectrum measured at 4.03 keV may be scaled up, in order to reproduce the expected peak intensities relative to other peaks measured under 7.0 kV excitation. FIG. 10 shows the calculated Bremsstrahlung X-ray intensity expected at the two excitation voltages, and the ratio between them at each energy, using the formulation given by Ebel [Reference 5]. This ratio is used in the scaling when the information from the two measured spectra is used together. Different acquisition times and/or emission currents can be used when measuring at different energy levels, to maximise signal-to-noise characteristics. The scaling of the respective spectra can be adjusted also take account of any differences in acquisition times and emission current, as well as the different shape of the intensity vs energy for different excitation voltages.

There remains a small gap in the reconstructed spectrum, around 4.0 to 4.2 keV, marked with an arrow 908, where it has not been possible to uncover any hidden diffraction peaks (and there is, in fact, a weak peak within this range for this particular sample). However, a similar reconstruction of the diffraction pattern without suppression of Ca—K fluorescence would have a gap which extends from 3.4 to 4.2 keV. Therefore a substantial gain in information has been obtained. Therefore we can say that the set of energies on which information is accessible from the two measured spectra together is greater than either of the measured spectra alone, even if it does not necessarily cover a single continuous range of energies leaving no gaps.

The reconstructed diffraction pattern forms the basis of analysis of the sample, along with the observation of the fluorescence peaks in each recorded spectrum. In some instances, the observation of diffraction peaks (or the absence of diffraction peaks) in the energy ranges which are otherwise obscured by fluorescence peaks may prove crucial to the identification of the minerals present in the sample.

Reconstruction of Diffraction Spectra—Example Lafayette

The second sample is intended to be representative of a specific meteorite known as "Lafayette", for which an analysis gave the following composition: siderite, $FeCO_3$, 57.0%; calcite, 35.8%; rhodochrosite, $MnCO_3$, 6.5%; and magnesite, $MgCO_3$, 0.8% [Reference 6]. Note that these mineral proportions are % by mole, but are converted to % by volume prior to simulation.

Figure 11:
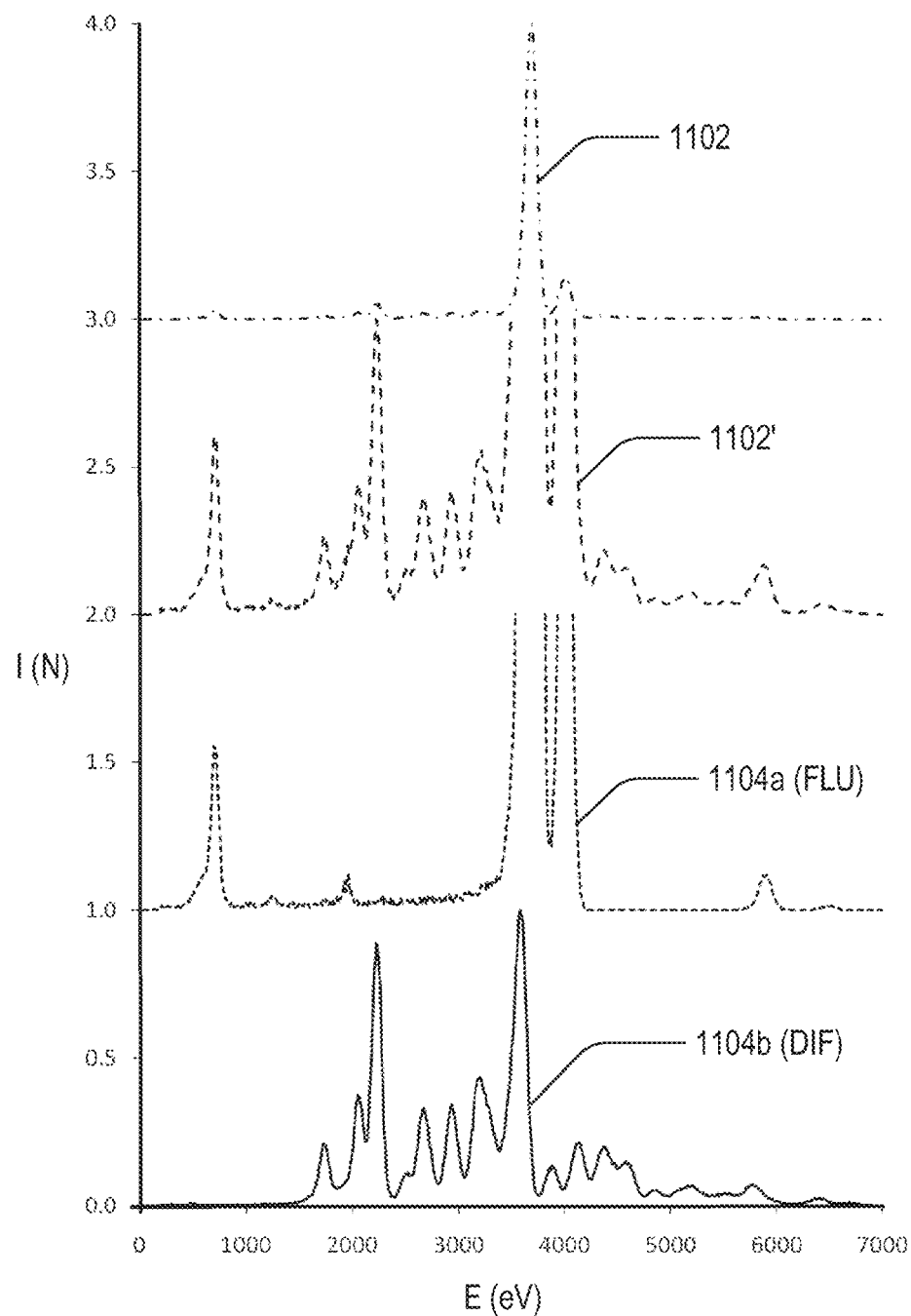
FIG. 11 shows simulations of the back-reflection EDXRD spectra of a Lafayette sample, for a tube excitation voltage of 7.0 kV.

FIG. 11 shows simulated traces 1102, 1102' (spectra) of the detected spectrum from the Lafayette sample, with a tube excitation voltage of 7.0 kV. Also plotted are simulated traces 1104a and 1104b which include diffraction-only and fluorescence-only contributions. As for the limestone sample, there are strong Ca—K fluorescence peaks, and an Mg—K peak. In addition, there are Mn—K peaks at 5.895 and 6.490 keV, although these are relatively weak. Note that the Fe—K absorption edge lies at 7.112 keV so the Fe—K fluorescence lines are not stimulated at all, but the peak near 0.7 keV is due to Fe-L and Mn-L fluorescence.

Figure 12:
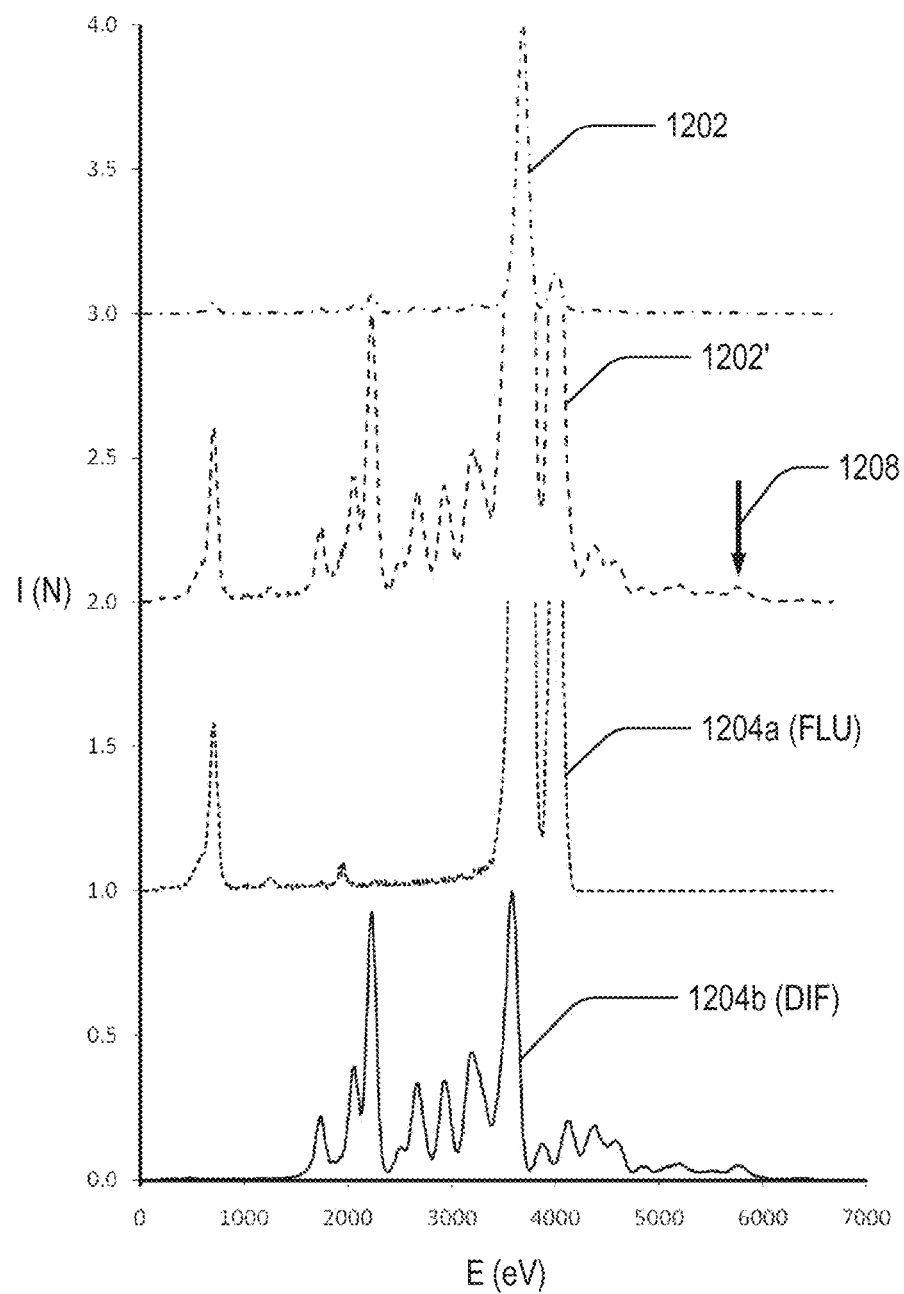
FIG. 12 shows simulations of the back-reflection EDXRD spectra of the Lafayette sample, for a tube excitation voltage of 6.535 kV.
Figure 13:
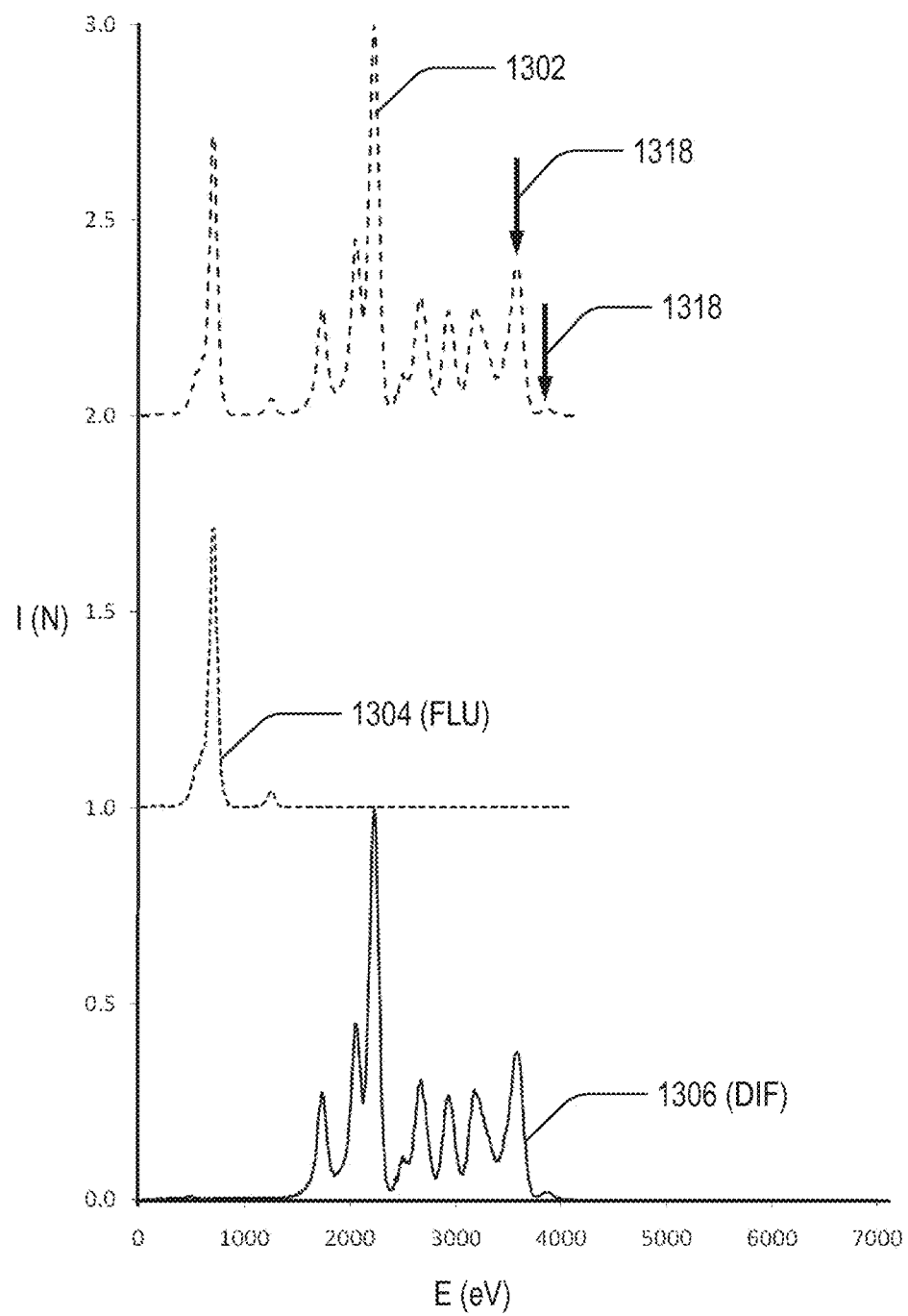
FIG. 13 shows simulations of the hack-reflection EDXRD spectra of the Lafayette sample, for a tube excitation voltage of 4.03 kV.

The Mn—K absorption edge lies at 6.537 keV, and so the corresponding fluorescence peaks can be suppressed by operating the X-ray tube at 6.535 kV. Simulations for this condition are shown in FIG. 12 which illustrates the simulations 1202, 1202' of the detected spectrum with a tube excitation voltage of 6.535 kV, along with simulations 1204a and 1204b which include diffraction-only and fluorescence-only spectra, while FIG. 13 shows simulations 1302, 1304 and 1306 with the tube operated at 4.03 kV in order to suppress the Ca—K fluorescence lines. In FIG. 12, the arrow 1208 indicates a diffraction peak which has been revealed by the suppression of the Mn—K fluorescence peaks. In FIG. 13, the arrows 1318 indicate diffraction peaks which have been revealed by suppression of the Ca—K fluorescence peaks.

Figure 14:
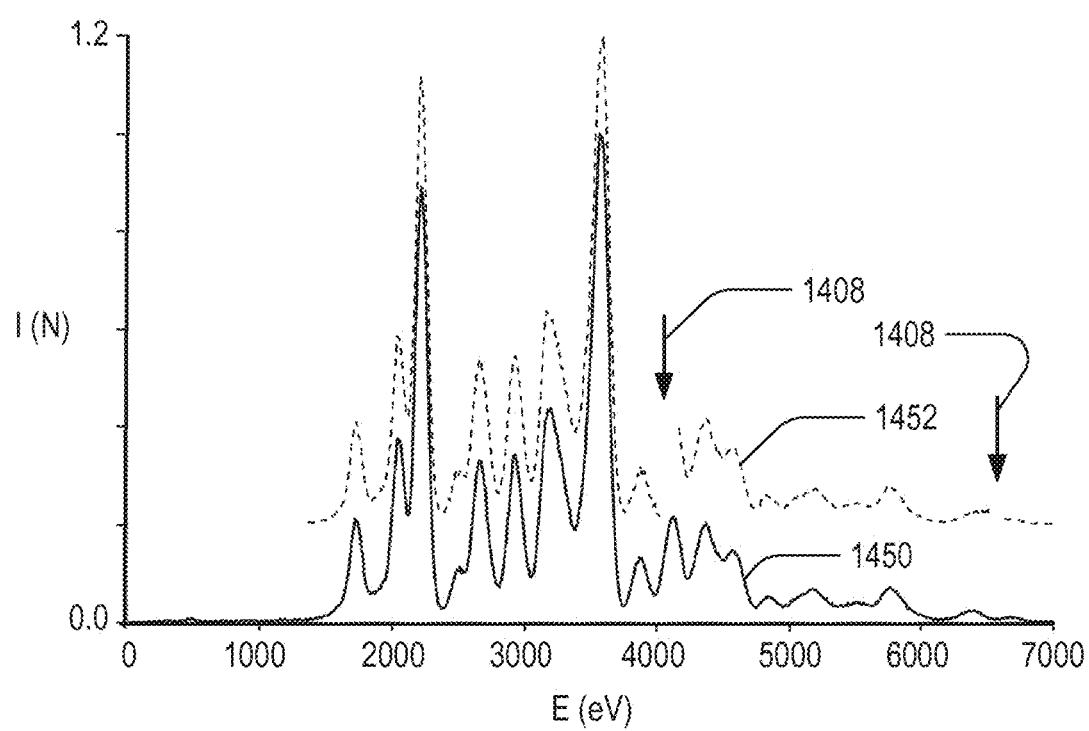
FIG. 14 shows simulations of the hack-reflection EDXRD spectra of the Lafayette sample, for a tube excitation voltage of 7.0 kV (lower trace), and a reconstructed diffraction pattern (upper trace) produced by a method according to an embodiment of the invention.

FIG. 14 shows the reconstructed diffraction pattern using the simulated spectra representing three spectra measured at the three different excitation voltages discussed above. The reconstruction procedure is essentially the same as described for the limestone sample, but the complete spectrum is synthesized not from two but from three spectra across three respective energy bands, so as to achieve the suppression of Mn—K fluorescence in addition to suppression of Ca—K. In FIG. 14, the original 'diffraction-only' simulation is shown as 1450 and a reconstructed diffraction pattern is shown as 1452. The arrows 1400 of FIG. 14 indicate two gaps in the reconstructed diffraction pattern.

Reconstruction of Diffraction Spectra—Example Basalt

Figure 15:
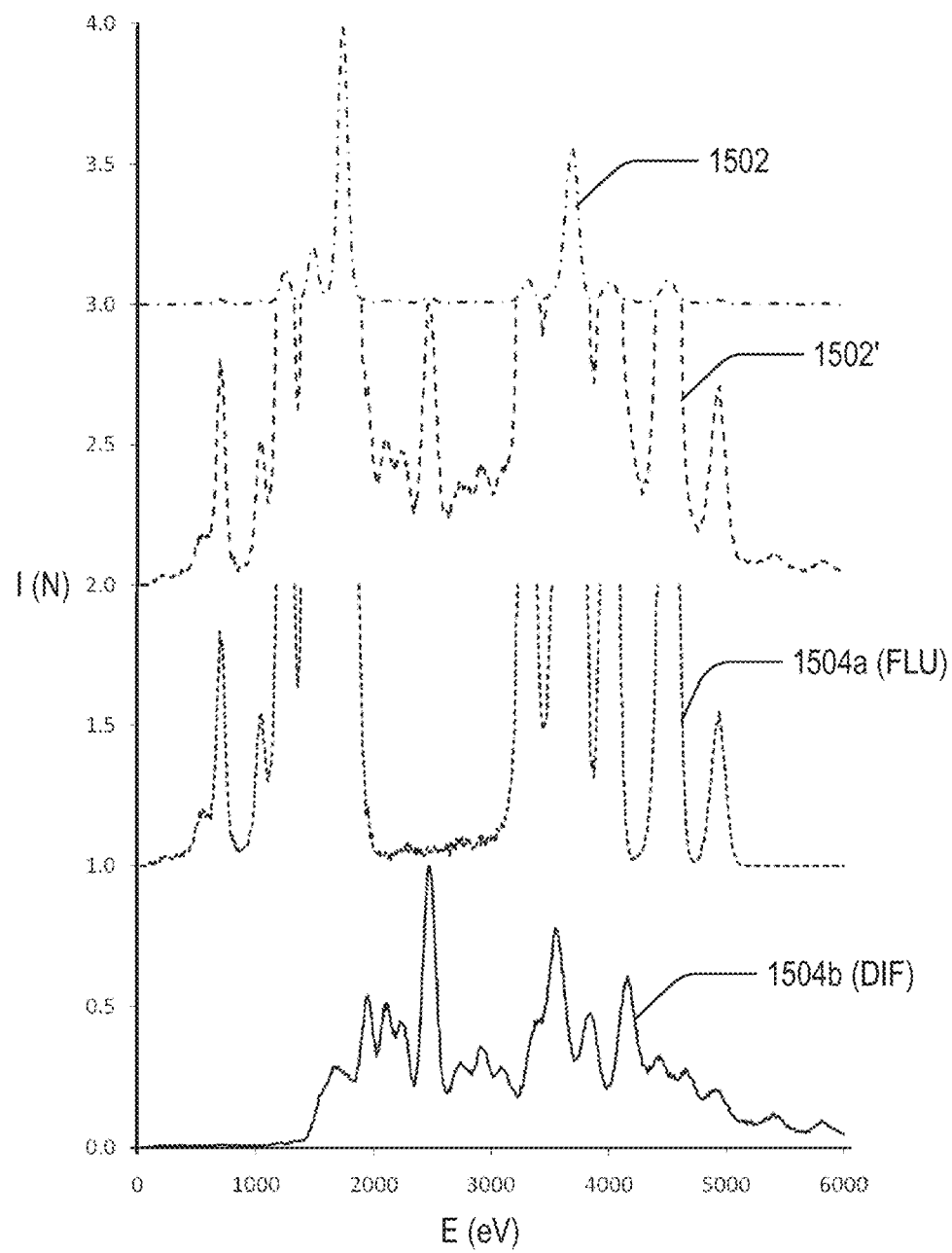
FIG. 15 shows simulations of the back-reflection EDXRD spectra of a basalt sample, for a tube excitation voltage of 7.0 kV.

FIG. 15 shows simulations of the back-reflection EDXRD spectra of a basalt sample, for a tube excitation voltage of 7.0 kV, which includes the simulations 1502 and 1502' of the detected spectrum along with simulations 1504a and 1504b of fluorescence-only and diffraction-only spectra respectively. The diffraction-only and fluorescence-only spectra (DIF, FLU) are not directly observable by a real instrument. The spectra have been normalized to the same vertical scale, except for the top-most trace which has been normalized to show the strongest fluorescence peaks. This sample corresponds to the "low-Al basalt" described in Reference 1. This sample consists of seven minerals: anorthite, $CaAl_2Si_2O_8$, 25.8%; diopside, $MgCaSi_2O_6$, 22.4%; albite, $NaAlSi_3O_8$, 17.8%; olivine, $(Mg,Fe)_2SiO_4$, 17.0%; orthoclase, $KAlSi_3O_8$, 8.0%; ilmenite, $FeTiO_3$, 4.8% and hypersthene (also known as ferrosilite), $(Mg,Fe)SiO_3$, 4.2%. These seven minerals contain a total of nine elements. Without the use of fluorescence suppression, the fluorescence peaks of the nine elements would effectively rule out the possibility of observing any diffraction peaks below 1.95 key and in the range approximately 3.15-5.05 keV.

Figure 16:
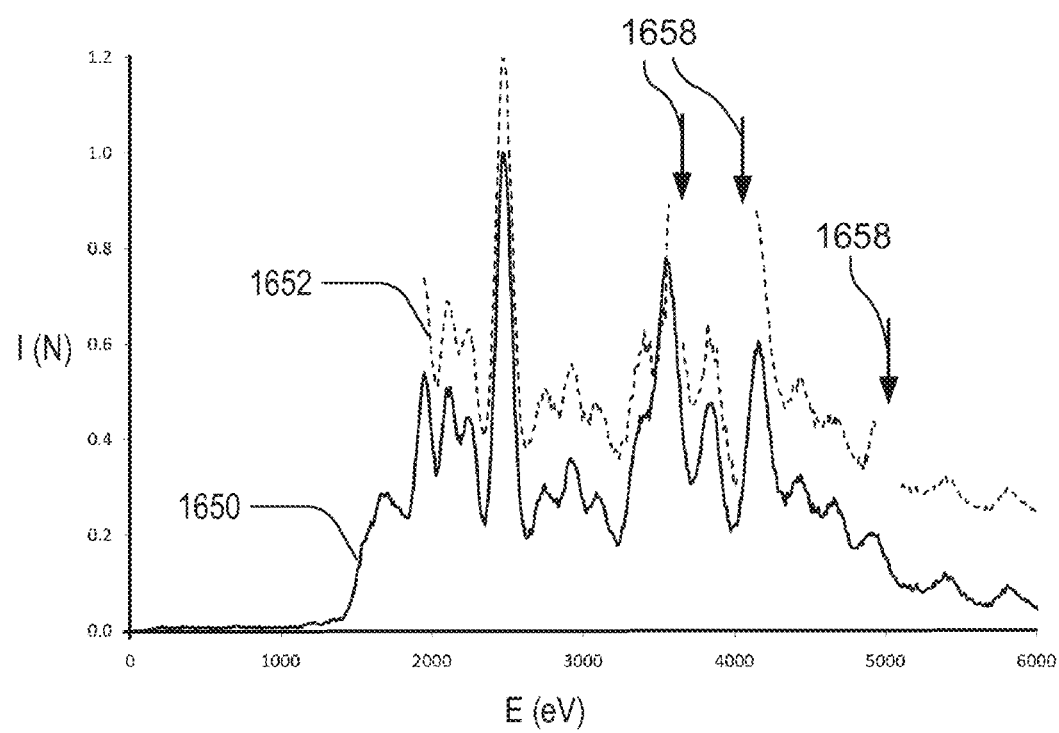
FIG. 16 shows simulations of the back-reflection EDXRD spectra of a basalt sample, for a tube excitation voltage of 7.0 kV (lower trace), and a reconstructed diffraction pattern (upper trace) produced by a method according to an embodiment of the invention.

FIG. 16 shows a reconstructed diffraction pattern compared to the diffraction-only simulation for 7.0 kV excitation. Suppression of the fluorescence peaks due to Ti, Ca and K was simulated using tube excitation voltages of 4.96 kV, 4.03 kV and 3.605 kV respectively, just below the K absorption edges of each element, with data acquisition times of three minutes each. These simulations are not shown separately for this sample. It will be seen that the diffraction pattern (spectrum) above 1.95 keV has been recovered, with just small gaps (marked by arrows 1658) near the absorption edges.

In principle, the process could be continued to lower energies, suppressing the Si, Al, Mg and Na fluorescence peaks which occur between 1 and 2 keV. However, this process yields diminishing returns for two reasons. Firstly, the energy ranges over which diffraction peaks can be uncovered become successively smaller towards lower energies. Secondly, the X-ray intensity output of the tube source is much smaller at the lower excitation voltages, extending the acquisition times needed for adequate signal strengths.

Experimental Demonstration of Fluorescence Suppression

The limestone sample used to generate the data for FIG. 3 was used again in an experiment to demonstrate the efficacy of suppression of fluorescence peaks. In this case, the 15 μm aluminium filter was replaced with a much thinner filter consisting of approximately 2 μm of polyimide coated with 1 μm of aluminium. This filter blocks the unwanted visible wavelengths of light without significantly attenuating X-ray intensity over the energy range of interest.

Figure 17:
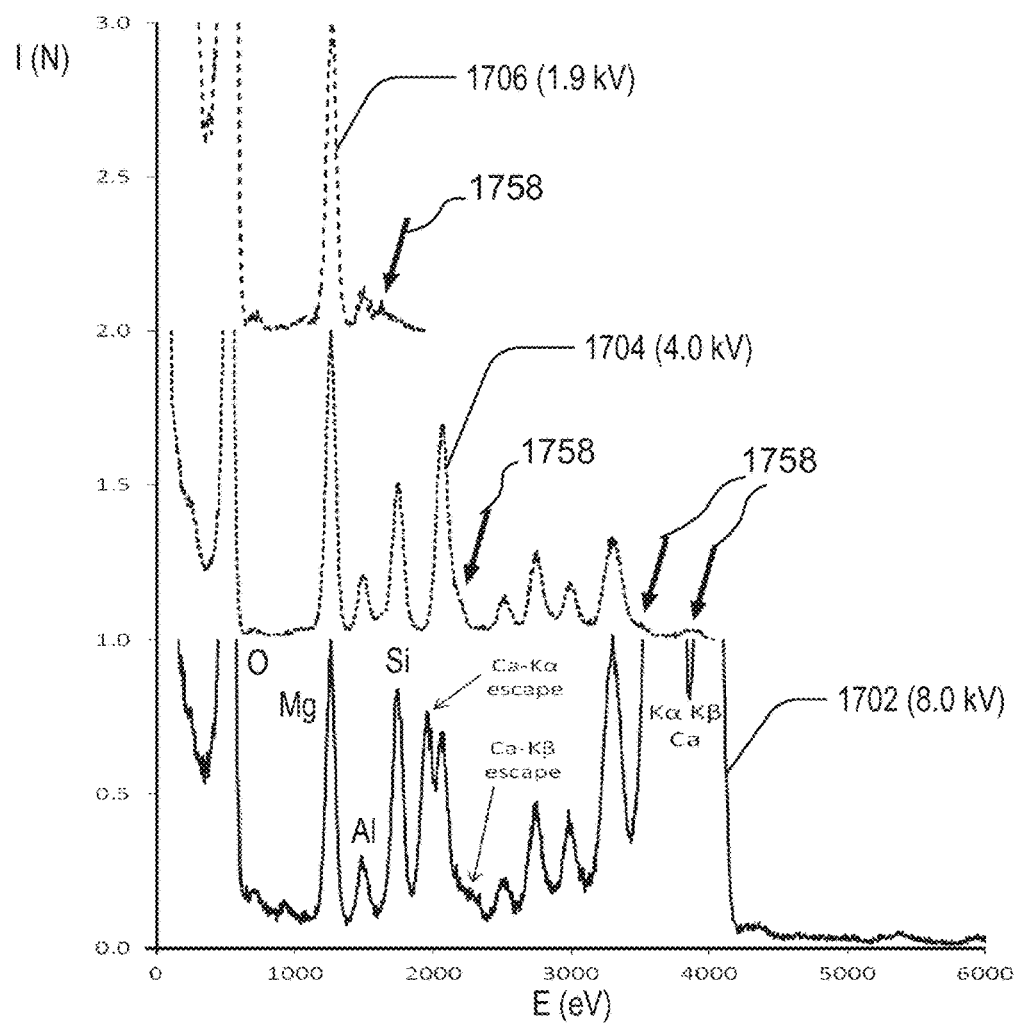
FIG. 17 shows experimental back-reflection EDXRD spectra of a limestone sample, for tube excitation voltages of 8.0, 4.0 and 1.9 kV (bottom trace to top trace, respectively)

FIG. 17 shows spectra 1702, 1704 and 1706 measured with respective tube excitation voltages of 8.0 kV, 4.0 kV (for Ca—K suppression) and 1.9 kV (for Si—K suppression). In FIG. 17, each trace 1702, 1704 and 1706 has been normalized in intensity to the Mg fluorescence peak. The fluorescence peaks are marked with the corresponding element. The "escape" peaks in FIG. 17 are detector artefacts associated with Ca—K peaks. Arrows 1758 of FIG. 17 indicate diffraction peaks which have been revealed by suppression of the Ca—K fluorescence peaks and their escape peaks (middle trace 1704) and suppression of the Si fluorescence peak (top trace 1706). The Si—K absorption edge lies at 1.84 keV, but there is only a small amount of Si present in the sample and so the fluorescence peak can be suppressed quite effectively even with the tube excitation voltage set slightly above the absorption edge. The suppression of Ca—K fluorescence works very well because the associated escape peaks are also suppressed, and the background in the range approximately 2 to 3.4 keV is also reduced.

Figure 18:
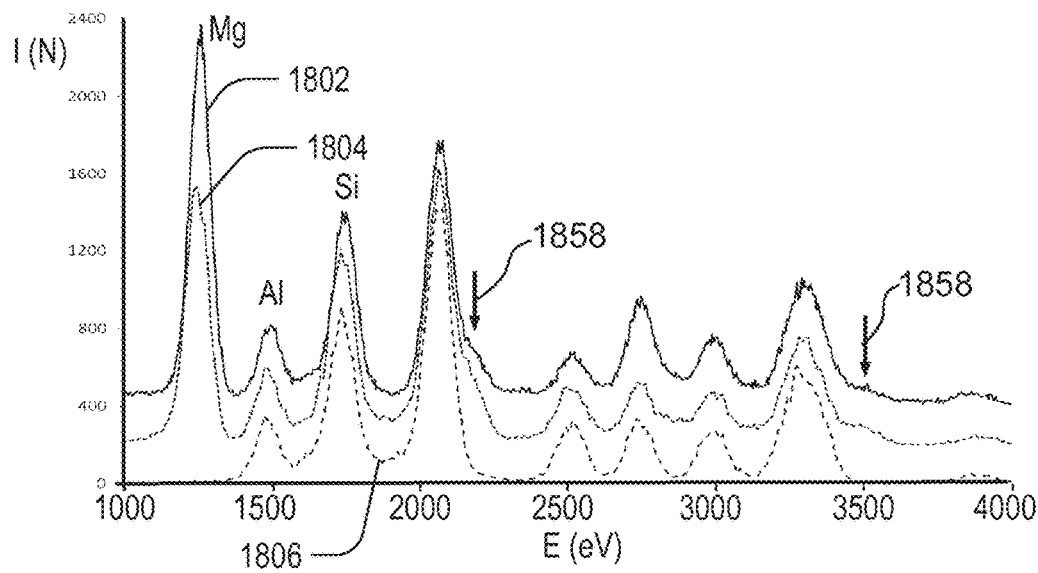
FIG. 18 shows simulations of comparison of the experimental spectrum (top trace) of the limestone sample, for tube excitation voltage of 4.0 kV to suppress Ca—K fluorescence.

FIG. 18 illustrates comparison of the reconstructed experimental spectrum (top trace 1802) of the limestone sample (tube excitation voltage of 4.0 kV to suppress Ca—K fluorescence) with model simulations which have been run in an attempt to reproduce the experimental data. The samples in the simulations consist of either calcite alone, or of 80% calcite and 20% dolomite. The bottom trace 1806 is a simulation for calcite only, and the middle trace 1804 is a simulation for 80% calcite and 20% dolomite (by volume). The arrows 1858 in FIG. 18 mark diffraction features in the experimental spectrum which are reproduced only by the inclusion of dolomite in the model. The inclusion of dolomite clearly reproduces a couple of diffraction features seen in the experimental spectrum (indicated arrows 1858 in FIG. 18), as well as explaining the Mg fluorescence peak. Thus, suppression of the Ca—K fluorescence peaks and associated artefacts has allowed the unambiguous identification of dolomite in the sample.

The example also illustrates that fluorescence signals are not entirely unwanted, but can aid in identification of the composition of a sample. It should be noted that pure calcite and dolomite contain no Al or Si. A minor amount of each element, 0.6% and 1.4% respectively, was added to the simulated sample compositions in order to reproduce the corresponding experimental fluorescence peaks. These additions have a negligible effect on the simulation of diffraction peaks, but the presence of these fluorescence peaks in the experimental data may be indicative of small amounts of unidentified minerals in the sample.

Implementation of Reconstruction

As mentioned in the description of the method of FIG. 6, the steps 604 & 608 that perform the selection of energies for capturing EDXRD spectra and the step 610 in which the measured spectra are combined, if desired, can be implemented in numerous ways to achieve XRF suppression. The process of suppression of X-ray fluorescence peaks in the above examples may be summarised by the following series of steps:

(a) Record a spectrum using an excitation voltage which is sufficiently high to capture diffraction peaks at the highest energy likely to be of interest. For back-reflection EDXRD, this is likely to be 7 kV or similar. (Implementation of steps 604, 606.)

(b) Identify probable fluorescence peaks in the spectrum on the basis of intensity, energy and occurrence of associated peaks, such as Kα and Kβ peaks with the expected relative intensities.

(c) Record an additional spectrum with the source excitation voltage set just below the absorption edge energy corresponding to the or each fluorescence peak selected for suppression. (Implementation of steps 608, 606.)

(d) Repeat step (c) for each fluorescence peak as desired.

(e) Select the energy range from each recorded spectrum expected to be free of fluorescence peaks, and scale the intensity relative to the spectrum recorded in step (a). (Implementation of step 610.)

(f) Combine the (scaled) spectra to form a single diffraction spectrum, which will then form the basis for further analysis using conventional methods. (Implementation of step 610.)

In some cases, fluorescence peaks in the spectrum recorded in step (a) may be of comparable intensity to the diffraction peaks, or weaker (for trace elements, for example), and these may be difficult to identify. A conservative approach to choosing which fluorescence peaks to suppress would be to compile a list of all elements which may feasibly be present in the sample and which fluoresce in the energy range of interest, and record additional spectra with maximum energies (e.g. tube excitation voltages) set just below the corresponding absorption edges. The apparatus controller 110 can be pre-programmed with the excitation voltages specific to a number of elements. These may be selected by an operator prior to operation, whereafter the controller proceeds automatically to acquire spectra for the different energy settings in sequence. The controller 110 can include a memory for storing developed sequences for subsequent recall and use.

Another approach could be to measure and record spectra across a whole range of excitation voltages in fine steps, rather than targeting specific expected absorption edges. This may make the measurement very time consuming and generate a lot of redundant data. However, it would allow a free selection of excitation voltages after the event, by computer processing without any need to re-measure. This form of 'virtual experiment' capability could be of interest for example where a sample will never be accessible again, and where its likely composition is completely unknown. It can also be used for training and research to devise optimum excitation sequences for future filed work.

The method described above specifies setting the excitation voltage "just below" an elemental absorption edge e.g. at 4.03 kV for suppression of Ca—K fluorescence peaks for which the corresponding absorption edge is at 4.034 keV. As an alternative, it may be possible to set the excitation voltage to a slightly higher value, for example 4.1 kV. Although the source will emit some X-rays above the Ca—K absorption edge, the flux of X-rays above this threshold will be very low (FIG. 10 shows how rapidly the X-ray flux drops towards the energy corresponding to the excitation voltage). The Ca—K fluorescence peaks will be correspondingly weak. By this means it may be possible to reduce or eliminate the gaps in the reconstructed diffraction patterns, such as the gap from 4.0 to 4.2 keV in FIG. 9.

In step (e) above, the relative intensities of the spectral output of the tube source at different excitation voltages may be derived by calculation using models available in the scientific literature, such as Reference 5, or by direct measurements of the X-ray tube being used. Depending on the details of the analysis procedure that follows (step 612), scaling of the selected spectra may potentially be skipped or simplified. For example, the selected spectra may be modelled directly, without any scaling applied, in order to determine the composition of the sample.

The composition of the partial spectra to produce a composite spectrum in step (f) can in principle be automated by a processor within the controller 110, or a separate processor forming part of the overall apparatus. A simple approach would be for such a processor to divide the composite spectrum into portions (energy sub-ranges) bounded by the set of energy settings for which spectra are available. Then, starting with the lowest energy setting, use the corresponding detected spectrum to define the composite spectrum in a sub-range extending up to a point corresponding to lowest energy setting. Then, taking the second lowest maximum energy setting, use the corresponding detected spectrum to define the composite spectrum in a second range extending up to a point corresponding to the second lowest energy setting. If there are several energy settings, proceed in this way until the highest energy setting spectrum has been used and a full set of ranges of the composite spectrum are filled (or left unfilled due to lack of data).

Where a composite spectrum is generated automatically, a user interface may be provided for adjusting parameters manually. For example, it may be desirable to allow some spectra to be disregarded due to poor signal quality, or to allow fine adjustment of the boundaries between spectra. As an addition or alternative to automatic synthesis, a graphical user interface can be constructed for assembling the composite spectrum under manual control. For example, a collection of spectra can be superimposed on a display, with controls for an operator to indicate a particular spectrum as the source for each portion of the composite spectrum.

The term 'wavelength-dispersive' is conventionally used to refer to spectrometer implementations using monochromators and the like, while 'energy-dispersive' is used to refer those where spectral resolution is limited by the resolving power of the detector. The difference is a matter of design choice in the context of the present disclosure, and the term 'energy resolved' as used herein can refer to either type. If an X-ray monochromator or spectrometer is used (to achieve greater spectral resolution, for example), the details of the measurement technique will need to be adapted as necessary. For example, if a monochromator is used between the X-ray source and the sample, the monochromator will be stepped through a series of settings in order to scan the X-ray energy (wavelength) and a spectrum will be recorded at each setting. The analysis procedure will also need to be adapted.

The samples which have been used to illustrate this method of fluorescence suppression are all geological in nature. However, the same method may be applied to any sample under investigation by EDXRD.

The examples shown have all involved suppression of elemental K-line fluorescence. The same principles can be followed to suppress the fluorescence arising from other series, such as L-lines. Implementation is complicated by the presence of three absorption edges, for L-lines, but the source energy can be tuned just below each edge in turn.

The design of the X-ray tube may be optimised in various ways to maximise the effectiveness of the fluorescence suppression method. For example, the anode material can be chosen in order to maximise the intensity of X-ray emission in the energy range close to the excitation energy. (The curves for copper in FIG. 10 indicate very weak signal as one approaches the excitation energy.) The formulation of the X-ray tube output given by Ebel [Reference 5] shows that this can be achieved by using an element with high atomic number, such as tungsten.

While specific embodiments of the invention have been described above, it will be appreciated that the invention may be practiced otherwise than as described. For example, the invention may be implemented partly in the form of a computer program containing one or more sequences of machine-readable instructions for controlling the apparatus to perform a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the spirit and scope of the claims set out below.

REFERENCES

1. G. M. Hansford, "Back-Reflection Energy-Dispersive X-Ray Diffraction: A Novel Diffraction Technique with Almost Complete Insensitivity to Sample Morphology", J. Appl. Cryst., 44, 514-525 (2011).
2. Graeme M. Hansford, "PoDFluX: a new Monte Carlo ray-tracing model for powder diffraction and fluorescence", Rev. Sci. Instrum., 80, 073903 (2009).
3. B. B. He, "Two-Dimensional X-Ray Diffraction", John Wiley & Sons, New Jersey (2009).
4. All X-ray fluorescence energies and absorption edge energies are taken from Kaye and Laby online: http://www.kayelaby.npl.co.uk/atomic_and_nuclear_physics/4_2/4_2_1.html
5. H. Ebel, *X-ray Spectroetry.*, 28, 255-266 (1999).
6. J. C. Bridges and M. M. Grady, Earth Planet. Sci. Lett. 176, 267-279 (2000).

The invention claimed is:

1. A method of inspecting a material sample by X-ray diffraction, the method comprising:

irradiating the material sample with a beam of X-ray radiation from a source with a range of photon energies;

obtaining at least one energy-resolved spectrum from radiation diffracted substantially back toward the source at diffraction angles greater than 155°; and processing the at least one energy-resolved spectrum to obtain information on spacing of crystal planes in the material sample, the obtained information being substantially independent of sample distance or morphology.

2. The method as claimed in claim 1, wherein a plurality of energy-resolved spectra are obtained using different settings of source energy, whereby at least one spectrum of the plurality of energy-resolved spectra excludes a fluorescence signal that is present in another spectrum of the plurality of energy-resolved spectra and the plurality of energy-resolved spectra are processed together to obtain information on the spacing of crystal planes in the material sample over a wider range of spacings than can be obtained from any one spectrum of the plurality of energy-resolved spectra on its own.

3. The method as claimed in claim 1, wherein the material sample is non-prepared rocks in their natural form.

4. An apparatus for use in performing energy-dispersive X-ray diffraction to determine characteristics of a material sample, the apparatus comprising:

a source arrangement for irradiating the material sample with a beam of radiation with a range of photon energies;

a detector for detecting radiation diffracted from a sample in a direction substantially back towards the source arrangement at diffraction angles greater than 155°;

a processor configured to:

resolve radiation detected by the detector into at least one energy-resolved spectrum; and process the at least one energy-resolved spectrum to obtain information on spacing of crystal planes in the material sample, the information on spacing of crystal planes in the material sample being substantially independent of sample distance or morphology.

5. The apparatus as claimed in claim 4, wherein the source arrangement is located behind the detector, such that the beam of radiation passes beside the detector or through and aperture in the detector to reach the material sample.

6. The apparatus as claimed in claim 4, wherein the source arrangement comprises a source of X-ray radiation that is controllable to restrict the maximum photon energy of radiation to different selected values.

7. The apparatus as claimed in claim 6, comprising a controller for automatically controlling the source arrangement and the detector to record a plurality of spectra using different maximum photon energies.

8. The apparatus as claimed in claim 4, wherein the detector substantially or completely surrounds a path of the beam of radiation.

9. The apparatus as claimed in claim 4, comprising:

an X-ray source;

a collimator comprising an aperture for passage of the beam of radiation; and an energy-resolving detector adjacent the aperture, the energy-resolving detector configured to receive diffracted radiation.

10. The apparatus as claimed in claim 4, comprising:

an X-ray source;

a collimator comprising an aperture for passage of the beam of radiation; and an energy-resolving detector that surrounds the aperture, the energy-resolving detector configured to receive diffracted radiation.

* * * * *